United States Patent [19]

Hausheer et al.

[11] Patent Number: 5,674,874
[45] Date of Patent: Oct. 7, 1997

[54] LACTONE STABLE FORMULATION OF 7-ETHYL 10-HYDROXY CAMPTOTHECIN AND METHODS FOR USES THEREOF

[75] Inventors: Frederick H. Hausheer; Kochat Haridas, both of San Antonio, Tex.

[73] Assignee: BioNumerik Pharmaceuticals, Inc., San Antonio, Tex.

[21] Appl. No.: 522,951

[22] Filed: Sep. 1, 1995

Related U.S. Application Data

[63] Continuation-in-part of Ser. No. 172,620, Dec. 22, 1993, Pat. No. 5,447,936.

[51] Int. Cl.[6] .................................................. A61K 31/475
[52] U.S. Cl. ........................................................... 514/283
[58] Field of Search .............................................. 514/283

[56] References Cited

U.S. PATENT DOCUMENTS

| | | | |
|---|---|---|---|
| 3,219,529 | 11/1965 | Nash . | |
| 3,699,230 | 10/1972 | Beauchamp et al. . | |
| 4,082,881 | 4/1978 | Chen et al. . | |
| 4,228,162 | 10/1980 | Luzzi et al. . | |
| 4,339,276 | 7/1982 | Miyasaka et al. | 491/22 |
| 4,399,282 | 8/1983 | Miyasaka et al. | 491/147 |
| 4,473,692 | 9/1984 | Miyasaka et al. | 546/48 |
| 4,545,880 | 10/1985 | Miyasaka et al. | 204/158 |
| 4,604,463 | 8/1986 | Miyasaka et al. | 544/60 |
| 4,713,246 | 12/1987 | Begum et al. | 514/27 |
| 4,734,284 | 3/1988 | Terada et al. . | |
| 4,778,891 | 10/1988 | Tagawa et al. | 546/18 |
| 5,004,758 | 4/1991 | Boehm et al. | 514/283 |
| 5,061,800 | 10/1991 | Wall et al. | 514/219 |
| 5,180,722 | 1/1993 | Kalsha | 546/48 |
| 5,225,404 | 7/1993 | Giovannella et al. | 514/81 |
| 5,227,380 | 7/1993 | Wall et al. . | |
| 5,447,936 | 9/1995 | Hausheer et al. | 514/283 |
| 5,468,754 | 11/1995 | Hausheer et al. | 514/283 |
| 5,496,830 | 3/1996 | Shapiro | 514/283 |
| 5,597,829 | 1/1997 | Hausheer | 514/283 |
| 5,604,233 | 2/1997 | Hausheer | 514/283 |
| 5,633,260 | 5/1997 | Hausheer | 514/283 |

OTHER PUBLICATIONS

Emerson, David L., et al; In Vivo Antitumor Activity of Two New Seven-Substituted Water Soluble Camptothecin Analogues; Cancer Research 55:603–609; Feb. 1995.

Gupta, Elora, et al; Metabolic Fate of Irinotecan In Humans: Correlation Of Glucuronidation With Diarrhea; Cancer Research 54:3723–3725, Jul. 1994.

Haas, Naomi B., et al.; Phase I/Pharmacokinetic Study of Topotecan by 24–Hour Continuous Infusion Weekly; Cancer Research 54:1220–1226, Mar. 1994.

Hinz, Hellmuth R., et al.; Pharmacokinetic of the In Vivo and In Vitro Conversion of 9–Nitro–20(s)–Camptothecin in Humans, Dogs, and Mice; Cancer Research 54:3096–3100, Jun. 1994.

Houghton, Peter J., et al; Therapeutic Efficacy of the Topoisomerase I Inhibitor 7–Ethyl–10–(4–[1–piperidino] –1–piperidino)–carbonyloxy–camptothecin against Human Tumor Xenografts: Lack of Cross–Resistance In Vivo in Tumors With Acquired Resistance To The Topoisomerase I Inhibotor 9–Dimethylaminomethyl–10–hydroxycampothecin; Cancer Research 53:2823–2829, Jun. 1993.

Luzzio, Michael J., et al; Synthesis And Antitumor Activity of Novel Water Soluble Derivatives Of Camptothecin As Specific Inhibitors of Topoisomerase I; Journal Of Medicinal Chemistry, 38:3,395–401.

Moertel, Charles G., et al; Phase II Study of Camptothecin (NSC–100880) in the Treatment Of Advances Gastrointestinal Cancer; Cancer Chemotherapy Reports Part 1 vol. 56, No. 1, Feb. 1972.

Rivory, Laurent P., et al; Kinetics of the In Vivo Interconversion of the Carboxylate and Lactone Forms of Irinotecan (CPT–11) and of Its Metabolite SN–38 in Patients; Cancer Research 54:6330–6333, Dec. 1994.

Supko, Jeffrey G., et al; Pharmacokinetics of the 9–Amino and 10, 1–Methylenedioxy Derivatives of Camptothecin in Mice; Cancer Research 53:3062–3069, Jul. 1993.

Wall, Monroe E., et al; Camptothecin And Taxol: Discovery To Clinic–Thirteenth Bruce F. Cain Memorial Award Lecture; Cancer Research 55:753–760, Feb. 1995.

Wall, Monroe E., et al; Camptothecin; AntiCancer Agents Based on Natura Product Models, Chapter 12, pp. 417–436, 1980.

Wall, Monroe E., et al; Plant Antitumor Agents. 30[1a,b] Synthesis And Structure Activity Of Novel Camptothecin Analogs; J. Med. Chem., 36:2689–2700, 1993.

*Primary Examiner*—Donald G. Daus
*Attorney, Agent, or Firm*—Thomas J. Dodd

[57] ABSTRACT

7-ethyl-10-hydroxy camptothecin (HECPT), an active metabolite of the camptothecin analog CPT-11 which is used as an anticancer drug, is poorly soluble in water. Because of its poor water solubility, HECPT has not been directly administered by parenteral or oral routes in human patients for the purpose of inhibiting the growth of cancer cells. There is also unpredictable interpatient variability in the metabolic production of HECPT from CPT-11 which limits the utility of CPT-11. This invention overcomes these limitations by teaching novel pharmaceutically acceptable lactone stable HECPT formulations for the direct administration of lactone stable HECPT formulations orally or parenterally to patients with various forms of cancer.

9 Claims, No Drawings

LACTONE STABLE FORMULATION OF 7-ETHYL 10-HYDROXY CAMPTOTHECIN AND METHODS FOR USES THEREOF

BACKGROUND OF THE INVENTION

This is a continuation-in-part application of U.S. patent application Ser. No. 08/172,620, filed Dec. 22, 1993 U.S. Pat. No. 5,447,936.

1. Field of the Invention 7-ethyl-10-hydroxy camptothecin (also known as "SN38" and referred to herein also as "HECPT") is one of the most potent camptothecin derivatives in either killing human cancer cells or inhibiting the growth of human cancer cells. Direct oral, topical or parenteral administration of HECPT to human patients with cancer has not been practical due to the very poor water solubility of HECPT; the inventors have determined that less than 1.0 microgram of HECPT will dissolve in 1 ml of Millipore filtered water. This invention teaches the direct administration of HECPT to human subjects to cancer by formulation compositions which comprise HECPT which is in the lactone form and can be administered orally, parenterally or topically. An additional utility of this invention is that the direct administration of lactone stable HECPT overcomes some of the major problems in interpatient variability and risks of treatment related drug toxicity and tumor mediated drug resistance associated with the administration or utility of CPT-11.

2. Description of the Related Art

A. Introduction

Camptothecin (CPT) was isolated in 1966 by Wall and Wani from *Camptotheca accuminata*, a Chinese yew. CPT was subsequently observed to have potent anti-cancer activity in preclinical studies and was introduced into human clinical trials in the early 1970's. CPT lactone was noted to be very poorly water soluble (approximately 0.1 microgram of drug dissolving in 1 ml of water) and in order for CPT to be administered in human clinical trials it was formulated with sodium hydroxide which resulted in hydrolysis of the lactone E ring of the camptothecin molecule to form the water soluble camptothecin carboxylate species. The sodium hydroxide formulation of CPT created a water soluble CPT species that permitted clinicians to administer larger doses of the drug to cancer patients undergoing Phase I and Phase II clinical trials. It was not until the 1980's that it was learned that the carboxylate species of CPT had approximately one-tenth of the antitumor potency of the lactone form. Clinical trials with sodium hydroxide formulated CPT were disappointing due to significant systemic toxicity and the lack of anti-tumor activity, and clinical studies of CPT were stopped in the early 1980's. Inventors predict that HECPT will exhibit similar pharmacologic behavior and clinical toxicities if it were administered to human subjects in the carboxylate form by the use of a sodium hydroxide formulation.

Further clinical development of camptothecin derivatives was not pursued until the 1980's. At that time it was reported that CPT had a unique mechanism of action involving the inhibition of DNA synthesis and DNA replication by interactions with the ubiquitous cellular enzyme Topoisomerase I (Topo I). This new information about the mechanism of action of camptothecin derivatives rekindled the interest in developing new Topo I inhibitors as anti-cancer drugs and subsequently several research groups began attempting to develop new camptothecin derivatives for cancer therapy. In general it was observed that camptothecin and HECPT were very poorly soluble in water (approximately less than one microgram of drug would dissolve in a milliliter of water) which limited the clinical utility of the drug because prohibitively large volumes (e.g. 5 or more liters) of water would be given to the patient in order to give an effective dose of the drug. Because of the poor solubility of camptothecin and many of its derivatives such as HECPT, a great deal of research effort was directed at generating new camptothecin derivatives that were more water soluble. It was also learned in the 1980's that treatment of camptothecins with an unaltered E-ring lactone with alkali metal hydroxides or carbonates would result in opening the camptothecin lactone E ring to form the carboxylate species, and the formation of the carboxylate species of camptothecin greatly increased the water solubility of the drug, but this advantage of increased drug water solubility for formulation was offset by a significant reduction in anti-cancer activity of the carboxylate species relative to the lactone species.

As stated earlier, camptothecin and many of its derivatives (Wall and Wani *Camptothecin ant Taxol: Discovery to Clinic-Thirteenth Bruce F. Cain Memorial Award Lecture* Cancer Research 55:753–760; 1995) are poorly water soluble and are reportedly poorly soluble in various organic solvents. There are numerous reports of newly created water soluble derivatives of camptothecin (Sawada, S. et al; Kingsbury, W. D. et al., Luzzio et al. *Synthesis and Antitumor Activity of Novel Water Soluble Derivatives of Camptothecin as Specific Inhibitors of Topoisomerase I* Jour. Med. Chem. 38:395–401; 1995) which were synthesized in an attempt to overcome some of the significant technical problems in drug administration of HECPT to human subjects with cancer. Several water soluble camptothecin derivatives have been synthesized in an attempt to address the poor water solubility and the difficulties in administration and toxicity to patients. Well known examples of these camptothecin derivatives include: 9-dimethylaminomethyl 10-hydroxy camptothecin (Topotecan), 7-[(4-methylpiperazino)methyl]-10,11-ethylenedioxy camptothecin, 7-[(4-methylpiperazino)methyl]-10,11-methylenedioxy camptothecin, and 7-ethyl-10-[4-(1-piperidino)-1-piperidino]carbonyloxy camptothecin (CPT-11). Other substituted camptothecin derivatives with different solubility and pharmacologic properties have been synthesized as well; examples of these camptothecin derivatives include 9-amino camptothecin and 9-nitro camptothecin which are both are poorly soluble in aqueous and nonaqueous media and have been tested in humans.

Of this diverse group of substituted camptothecin derivatives undergoing human clinical development, CPT-11 is one of the most extensively studied in Phase I and Phase II clinical trials in human patients with cancer. It is noteworthy that CPT-11, which is a water soluble prodrug, is biologically inactive and requires activation by a putative carboxylesterase enzyme. The active species of CPT-11 is the depiperidenylated 7-ethyl-10-hydroxy camptothecin, also known as SN38 (claimed in Miyasaka et al. U.S. Pat. No. 4,473,692 (1984)), which is also described as HECPT for the purposes of this invention. SN38 is a toxic lipophilic metabolite which results from in vivo bioactivation of CPT-11 by a carboxylesterase enzyme. SN38 is very poorly soluble in water and has not been directly administered to human patients with cancer. Recently it has been reported in human patients that SN38 undergoes further metabolism to form a glucuronide species which is an inactive form of the drug with respect to antitumor activity, and also appears to be involved in producing human toxicity (diarrhea, leukopenia) and substantial interpatient variability in drug levels of the free metabolite and its glucuronide.

CPT-11 has been in human clinical trials in the United States, Europe and Japan and several patient deaths due to drug toxicity have been reported in association with the use of CPT-11. The Miyasaka et al. patents (U.S. Pat. No. 4,473,692 (1984) and 4,604,463 (1986)) state that the object of their invention is to "provide 10-substituted camptothecins which are strong in anti-tumor activity and possess good absorbability in living bodies with very low toxicity" (Miyasaka et al. U.S. Pat. No. 4,473,692 (1984) and "to provide new camptothecin derivatives which are strong in anti-tumor activity and possess good solubility in water and an extremely low toxicity" (Miyasaka et al. U.S. Pat. No. 4,604,463 (1986). Having multiple human patient deaths and serious patient toxicity which are clearly due to the administration and use of CPT-11 and its metabolite, 7-ethyl-10-hydroxy camptothecin (SN38) is clearly not a good outcome with the applications of these inventions which are claimed compositions in the Miyasaka et al. inventions. It is notable that tremendous interpatient variability with regard to drug levels of various species, their metabolism, certain pharmacokinetic properties and variable toxicity has been reported with the use of CPT-11 in human subjects with cancer. Parenteral administration of CPT-11 can achieve micromolar plasma concentrations of CPT-11 that, through metabolism to form SN38, can yield nanomolar concentrations of the active metabolite SN38. It has recently been reported in human subjects that SN38 undergoes further metabolism to form the SN38 glucuronide (Gupta et al. *Metabolic Fate of Irinotecan in Humans: Correlation of Glucuronidation with Diarrhea.* Cancer Research 54:3723–3725). The inventors believe that this metabolic conversion of CPT-11 is important since there is reportedly tremendous variability in the conversion of CPT-11 (micromolar plasma levels) to SN38 (nanomolar plasma levels) and further interpatient variability in the metabolism of SN38 to form SN38 glucuronide in human subjects (Gupta et al. *Metabolic Fate of Irinotecan in Humans: Correlation of Glucuronidation with Diarrhea.* Cancer Research 54:3723–3725; 1994 and Ohe, Y. et al., *Phase I Study and Pharmacokinetics of CPT-11 with 5-Day Continuous Infusion.* JNCI 84(12):972–974, 1992). Since the amount of CPT-11 and SN38 metabolized is not predictable in individual patients, this poses significant clinical limitations and risk of life-threatening drug toxicity to patients due to five possible mechanisms: (1) due to conversion of greater amounts or more rapid conversion per unit of time of CPT-11 to SN38, (2) inactivation of SN38 by glucuronidation, (3) by conversion of SN38 glucuronide to free SN38, (4) lack of or reduced anti-tumor activity due to the conversion of lesser amounts of CPT-11 to form SN38, or (5) lack of anti-tumor activity by more rapid and extensive conversion of SN38 to form the glucuronide species. It is important to note that doubling the plasma concentration of the potent CPT-11 metabolite (SN38) in a patient may result in significant toxicity because free SN38 exhibits anti-tumor activity at nanomolar concentrations.

As mentioned previously, several patient deaths have been reported in Japan in association with the use of CPT-11 (Drug & Market Development 4:p 203; 1994). These human deaths appear to be related to the unpredictable nature of metabolic conversion of CPT-11 and SN38 glucuronide to form free SN-38. The present invention overcomes these limitations and has significant utility in patient safety because this invention allows the direct administration and thus direct pharmacologic control of SN38 in the active lactone form and will have superior bioavailability relative to CPT-11.

The instant invention is also aimed at overcoming other important limitations in bioavailability and pharmacokinetics and common tumor mediated drug resistance mechanisms reported with the use of CPT-11 (Wall and Wani Cancer Research 55:753; 1995 and Potmesil Cancer Research 54:1431; 1994, Supko and Malspeis Cancer Research 53:3062; 1993 and Hinz et al. Cancer Research 54:3096; 1994). This invention teaches new HECPT lactone compositions which have greater clinical utility for treating human subjects with cancer based on several chemical and pharmacologic properties. First, the inventors believe that the direct administration of HECPT will result in clinical advantages over these other camptothecin derivatives because of relatively superior tissue penetration, bioavailability and tissue retention. The inventors believe that in many instances it is more useful and convenient to administer the drug orally to cancer patients, and the superior lipid solubility and small molecular size of HECPT compositions will have a greater advantage over water soluble camptothecin derivatives in the setting of oral administration. As mentioned earlier, the instant invention involving the formulation of HECPT which can be administered in the lactone form overcomes much of the major interpatient pharmacokinetic variability and risk associated with the use of a prodrug as in the case of CPT-11.

SN38 (also known as "7-ethyl-10-hydroxy camptothecin" or "HECPT") as formulated in the present invention has substantial utility since it does not require metabolic activation to exert tumor cytotoxicity and exhibits potent anti-tumor activity against common types of human cancer including but not limited to cancers of the lung, breast, prostate, melanoma and colon. HECPT as described by the instant invention possess Topoisomerase I inhibitory activity similar to that of other camptothecin derivatives. Until now, HECPT which has poor water solubility have not been pursued in the clinic because of limitations in pharmaceutical formulations and methods of use. These HECPT compositions can be readily formulated in a pharmaceutically acceptable manner by dissolving the HECPT composition an organic solvent or a mixture of organic solvents which have a high degree of physiologic safety, thus allowing the direct administration of these new classes of compounds as active species to cancer patients. In view of very limited potentially active camptothecin derivatives in poorly water soluble and highly lipid soluble category, there clearly remains a large unmet need to develop new methods to administer HECPT which does not require metabolism to active species and is less susceptible to clinically important types of drug resistance in tumors. These new compositions of matter claimed in the present invention address these unmet needs and can, in addition to topical and parenteral routes of administration, be administered orally which is more convenient for many human patients undergoing treatment for cancer.

The inventors, entirely through their own efforts, have made a surprising discovery that HECPT posses the following characteristics in their new formulations:

1. Potent antitumor activity (nanomolar activity in inhibiting the growth of human tumor cells in vitro)

2. Potent inhibition of human Topoisomerase I

3. Lack the requirement for metabolic drug activation

4. Can be administered as the lactone species directly to human patients for the purpose of treating a variety of cancers 5. Small molecular weight (e.g., MW<500)

6. Highly soluble in organic pharmaceutical solvents including dimethylacetamide and dimethylisosorbide or cosolvents (e.g., dimethyl sulfoxide, PEG 300–400).

7. Oral, in addition to parenteral and topical, administration to human subjects with cancer For the purpose of this invention which supports the absolute novelty of the present invention which teaches the methods to formulate HECPT in a manner which is useful for the purposes to administer HECPT to patients with cancer it is also important to note that Miyasaka et al. (U.S. Pat. No. 4,399,282) state the following:

As camptothecin itself carries a lactone ring as ring E, this lactone ring is opened by the action of an alkaline reagent. Similarly, when the camptothecin derivatives of the present invention are treated, for example with an alkali metal hydroxide or carbonate in a conventional manner at room temperature or at an elevated temperature, the derivatives can be converted into corresponding alkali metal salt such as the sodium, potassium or lithium salt. These salts are all water-soluble and are of course involved in the scope of this invention. These salts are easily converted again into the free form by the action of an acid or in vivo. Thus, the pharmacological effect of the camptothecin derivatives is not influenced by such treatments. A preferable salt of the camptothecin derivative is the sodium or potassium salt."

The inventors believe that this teaching by Miyasaka et al. differs significantly with respect to HECPT (also known as SN38 and 7-ethyl-10-hydroxy camptothecin) containing an unmodified 20(S) E ring lactone since the pharmacological behavior and antitumor activity of HECPT will be profoundly and adversely influenced by such treatments as follows. By treating camptothecins, such as HECPT, with alkali metal hydroxide or carbonate the camptothecin derivative will form the camptothecin carboxylate species by base-mediated hydrolysis of the E-ring lactone. The resulting camptothecin derivative carboxylate species will be water soluble and have substantially reduced antitumor activity and adversely altered pharmacokinetic behavior and is not, in the opinion of the inventors, the preferred form of the drug to administer to patients. The inventors believe that only the lactone E-ring species of HECPT is the preferred form of the drug for administration to human subjects with cancer. Further, the inventors predict that there will be a tremendous difference in the pharmacological properties and behavior of HECPT administered as the intact lactone E-ring species versus HECPT administered as the carboxylate species of camptothecin derivative in vivo in human subjects. The inventors predict that the carboxylate species of HECPT will have a significantly shorter plasma half life and will have a greater amount of excretion via the renal route. This prediction is supported by pharmacologic evidence from clinical studies in humans and other mammalian species receiving sodium camptothecin, 9-amino camptothecin and Topotecan (Supko and Malspeis *Pharmacokinetics of the 9-amino and 10,11-Methylenedioxy Derivatives of Camptothecin in Mice* Cancer Research 53:3062–3069; 1993, Haas et al. *Phase I/Pharmacokinetic Study of Topotecan by 24-Hour Continuos Infusion Weekly* Cancer Research 54:1220–1226; 1994). It is also well known in the art that, in general, water soluble forms of a drug will not penetrate lipid membranes of tissues as well as lipid soluble drugs. Accordingly, the carboxylate species of HECPT are predicted to have lesser bioavailability relative to HECPT which is administered as the intact lactone E ring species when administered to human patients. Lesser bioavailability of the drug will lead to a reduction in the effectiveness of treatment and may increase the risk of patient toxicity.

Since our present art has the objective of creating new and useful formulations of HECPT suitable for nonaqueous oral, topical and parenteral formulations, from the standpoint of improving cancer therapy, this new art teaches new methods to produce optimal drug formulations based on the use of either dimethylacetamide or dimethyl isosorbide as the starting primary excipients used to make solutions or suspensions of HECPT which are suitable for oral or parenteral administration to human subjects with cancer.

SUMMARY OF THE INVENTION

Brief Summary of the Invention

It is an object of the present invention to allow the direct parenteral, oral or topical administration of HECPT to human subjects with cancer. The instant invention has the following useful properties:

1. Potent antitumor activity (nanomolar activity in inhibiting the growth of human tumor cells in vitro)

2. Potent inhibition of human Topoisomerase I

3. Lack the requirement for metabolic drug activation

4. Can be administered in the lactone species directly to human patients for the purpose of treating a variety of cancers 5. Small molecular weight (e.g., MW<500)

6. HECPT has been observed entirely by the efforts of the inventors to be highly soluble (up to about 5 mg/ml in dimethylacetamide and up to about 2 mg/ml in dimethylisosorbide 7. HECPT dissolved or suspended in dimethylacetamide or dimethylisosorbide can be further mixed with additional organic pharmaceutical solvents and excipients including, without restriction or limitation, polyethylene glycol (PEG 300 or PEG 400), and mineral acids including hydrochloric acid, phosphoric acid and organic carboxylic acids including citrate, fumarate, succinate, malate, or taurocholic acid and cosolvents such as polysorbate.

8. Oral, in addition to parenteral and topical, administration of HECPT formulations to human subjects with cancer This invention also involves the formulation of lactone stable HECPT to treat cancer in humans. In the case of intravenous administration of HECPT, several schedules and various dosages produce sufficient levels of lactone stable HECPT to yield beneficial antitumor effects in humans. The effective levels of HECPT are reasonably safe in terms of the incidence and severity of specific side effects that may occur with administration and are acceptable within standard medical practice for patients undergoing treatment for cancer.

Direct administration of HECPT in the lactone form is likely to offer several important clinical advantages over administration of CPT-11. For example:

(1) direct administration of HECPT allows the clinician to tailor the administration of the active cytoxic species (lactone stable HECPT) to suit the patient's tolerance and safety;

(2) direct administration of HECPT overcomes interpatient variability which may be due to polymorphism of key enzyme(s) in the metabolism of CPT-11 to HECPT; and (3) clinicians can more consistently optimize the drug dosage and schedule to achieve the maximum tolerated dose of HECPT (the active species) which is likely to lead to the most beneficial clinical anti-cancer effect.

Regarding the clinical utility of HECPT for the treatment of human cancer, this invention provides the following:

(1) Oral and parenteral formulations consisting of either solutions or suspensions of lactone stable HECPT;

(2) antitumor compositions comprising lactone stable HECPT;

(3) use of HECPT for the treatment of localized complications of cancer by direct administration via instillation into various body cavities.

Definitions

For this invention, certain words and phrases are defined as follows:

"Lactone stable HECPT" is defined as 7-ethyl-10-hydroxy camptothecin, also known as SN38, wherein the E-lactone ring form of HECPT molecule is the predominant (greater than 99%) chemical species in the formulation. For this invention, "SN38", "lactone stable HECPT", "BNPI-1028" and "HECPT" are used interchangeably.

"Routes of administration" means any conventional method for administering aqueous or other formulations or drugs to a human patient.

"Stable" means that the solution will not undergo major (>1.0%) chemical conversion within a reasonable period of time (dependent upon the final pH of the formulation mixture).

The word "about" when used for pH, concentrations, etc. is defined as plus or minus 1%.

"Approximately" is defined to include a range of plus or minus 1%.

"Unacceptable toxicity" is defined by World Health Organization (WHO) as grade 3 non-hematologic toxicity excluding nausea and vomiting and grade 4 vomiting or hematologic toxicity according to the National Cancer Institute common toxicity criteria. Since some clinical drug toxicity is anticipated in routine clinical oncology practice, appropriate treatment will be used to prevent toxicity (e.g., nausea and vomiting) or ameliorate signs and symptoms if they are observed (e.g., diarrhea). For example, antiemetics will be administered for nausea and vomiting, antidiarrheals for diarrhea, and antipyretics for fever. Appropriate dosages of steroids/antihistamines will also be used to prevent or ameliorate any anaphylactoid toxicity if an anaphylactoid reaction is observed.

"Parts by weight" is defined as the amount of a specified component contained within a formulation which is based on the total weight of the formulation. For example a formulation containing dimethylacetamide 5000 parts by weight, citric acid 100 parts by weight, PEG 300 1000 parts by weight and ethyl alcohol 1000 by weight would mean that the formulation contains 5000 mg of dimethylacetamide, 100 mg of citric acid, 1000 mg of PEG 300 and 1000 mg of ethanol. The total weight of this formulation would be 7,200 mg or 7.2 g.

"A formulation" is a solution or suspension or solid composition which contains a drug product which is administered to a patient with cancer. For this invention, solution, formulation, and suspension are used interchangeably.

HECPT Dissolved in Dimethylisosorbide or Dimethylacetamide and Acid

An aspect of the claimed invention is a 7ethyl-10-hydroxy camptothecin (HECPT) solution comprising HECPT dissolved in dimethylisosorbide (DMI or dissolved in dimethylacetamide (DMA). Also embodied in this invention is a formulation comprising HECPT and DMA or HECPT and DMI.

An aspect of the claimed invention is a 7ethyl-10-hydroxy camptothecin (HECPT) formulation comprising HECPT, dimethylisosorbide (DMI), and a pharmaceutically acceptable acid or dimethylacetamide (DMA), and a pharmaceutically acceptable acid.

An aspect of this invention is a 7ethyl-10-hydroxy camptothecin formulation comprising 7ethyl-10-hydroxy camptothecin, dimethylacetamide, and a pharmaceutically acceptable acid selected from the group consisting of a carboxylic acid, a mineral acid and an admixture of a carboxylic acid and a mineral acid. An embodiment of this formulation is wherein said formulation has between about 0.1 mg and about 15.0 mg activity of 7ethyl-10-hydroxy camptothecin per ml of formulation and wherein said acid is in an amount sufficient to result in a final pH of between about 2.0 and about 6.0; also wherein said acid is in an amount sufficient to result in a final pH of between about 3.0 and about 5.0.

Also, this formulation is parenterally administered to a human patient with cancer. The parenteral formulation has between about 0.1 mg and about 5.0 mg activity of 7ethyl-10-hydroxy camptothecin per ml of formulation.

Also, this formulation is orally administered to a human patient with cancer and the formulation has between about 0.1 mg and about 20.0 mg activity of 7ethyl-10-hydroxy camptothecin per ml of formulation.

Further embodied is a carboxylic acid selected from the group consisting of tartaric acid, citric acid, succinic, fumaric, maleic acid, gluconic acid, ascorbic acid, taurocholic acid, and taurocholic acid in an admixture with citric acid and wherein said carboxylic acid is selected from the group consisting of citric acid and taurocholic acid in an admixture with citric acid.

Yet another embodiment is wherein said mineral acid is selected from the group consisting of hydrochloric acid, and phosphoric acid or the acid is an admixture of a carboxylic acid and mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid.

Another aspect of this invention is a 7ethyl-10-hydroxy camptothecin formulation consisting essentially of 7-ethyl-10-hydroxy camptothecin, dimethylacetamide and a pharmaceutically acceptable acid, wherein said acid is a carboxylic acid selected from the group consisting of tartaric acid, citric acid, succinic, fumaric, maleic acid, gluconic acid, ascorbic acid, taurocholic acid, and taurocholic acid in an admixture with citric acid. Also, this formulation is administered orally to a human patient with cancer and wherein said acid is taurocholic acid in an admixture with citric acid. Yet another embodiment is wherein the acid is citric acid and the formulation has between about 0.1 mg and about 15.0 mg activity of 7ethyl-10-hydroxy camptothecin per ml of formulation.

Another aspect of this invention is a 7ethyl-10-hydroxy camptothecin formulation comprising 7ethyl-10-hydroxy camptothecin, dimethylacetamide and a pharmaceutically acceptable acid, wherein said acid is selected from a group consisting of a mineral acid and an admixture of a mineral acid with a carboxylic acid, wherein said mineral acid is selected from the group consisting of phosphoric acid, and hydrochloric acid and wherein said admixture is selected from the group consisting of taurocholic acid in an admixture with phosphoric acid, taurocholic acid in an admixture with hydrochloric acid, citric acid in an admixture with phosphoric acid and citric acid in an admixture with hydrochloric acid. This formulation may be administered parenterally to a human patient with cancer and said formulation has between about 0.1 mg and about 5.0 mg activity of 7ethyl-10-hydroxy camptothecin per ml of formulation.

Also, this formulation may be administered orally to a human patient with cancer, wherein said acid is selected from the group consisting of taurocholic acid in an admixture with phosphoric acid and taurocholic acid in an admixture with hydrochloric acid and wherein said oral formulation has between about 0.1 mg and about 20.0 mg activity of 7ethyl-10-hydroxy camptothecin per ml of formulation.

Another aspect of this invention is a 7ethyl-10-hydroxy camptothecin formulation comprising 7ethyl-10-hydroxy camptothecin and dimethylacetamide wherein said formulation has between about 0.1 mg and about 5.0 mg 7-ethyl-10-hydroxy camptothecin activity per one milliliter of dimethylacetamide.

The 7ethyl-10-hydroxy camptothecin (HECPT) solution or formulation is prepared by dissolving the desired components in dimethylisosorbide (DMI) or dimethylacetamide (DMA). Dimethylisosorbide has been used as solvent for muscle relaxants (U.S. Pat. No. 3,699,230), tetracyclines (U.S. Pat. No. 3,219,529), aspirin (U.S. Pat. No. 4,228,162), and steroids (U.S. Pat. No. 4,082,881). DMI and DMA have very good toxicity profiles and are miscible with ethanol, propylene glycol, isopropyl myristate, water, diethyl ether, corn oil, acetone, cottonseed oil, and the like.

An object of the present invention is to provide a solution, formulation or suspension of HECPT in DMI or DMA. A concentrated solution is particularly useful as a small volume parenteral formulation or a concentrated suspension is useful as a filling formulation for gelatin capsules. The solution may also be formulated for parenteral use providing a useful and practical means to dissolve the drug prior to administration and, if desired, the non-aqueous formulation can be further diluted with water to allow a parenteral infusion of the drug.

The present invention is prepared by dissolving the desired components in DMI or DMA and the resulting solution is then filtered and the filtrate collected. The amount of HECPT contained in the solution of this invention is not specifically restricted but may be any amount convenient for pharmaceutical purposes, and may be selected according to the dosage to be prepared. A preferred capsule filling solution contains from about 0.1 mg to about 15.0 mg of HECPT activity per ml of solution.

As a preferred embodiment of the claimed invention, the 7ethyl-10-hydroxy camptothecin solution is prepared by dissolving the desired components in dimethylisosorbide (DMI) or dimethylacetamide (DMA) in the presence of a pharmaceutically acceptable acid.

A pharmaceutically acceptable acid is preferably included in the solutions or formulations of the present invention. Any pharmaceutically acceptable acid may be used; for example mineral acids such as hydrochloric acid or phosphoric acid; and organic carboxylic acids, such as tartaric, citric, succinic, fumaric, maleic acids, gluconic acid, ascorbic acid, taurocholic acid or taurocholic acid in an admixture with citric acid. An organic carboxylic acid is preferred, and citric acid is most preferred. The amount of acid used should be sufficient to result in a solution or suspension which when administered to a patient has a final pH in the range of about 2.0 to about 6.0. A more preferred pH range of the final drug formulation for administration to patients is between about 3.0 to about 5.0. Organic carboxylic acids and mineral acids such as citric acid, hydrochloric acid and phosphoric acid are all useful for these formulations, alone or in any combination, in producing lactone stable HECPT formulations which are acidified with or without further dilution with water. Additionally, taurocholic acid is can be used alone or in combination with other acids including, in any combination, citric acid, hydrochloric acid or phosphoric acid when an oral formulation of HECPT is desired.

In the formulations provided by the instant invention, HECPT is both soluble and maintained in its E-ring lactone form. The non-enzymatic conversion of the pH labile E ring from the closed lactone (active) to the open carboxylate form (inactive) is reduced by formulating HECPT under acidic pH conditions (<5.0). Thus, a water soluble acid is included to assure that an acidic pH value is maintained upon dilution in aqueous environments to form the micellar solution. Examples of preferred solid water-soluble organic carboxylic acids effective in this invention include citric, gluconic, maleic, tartaric, or ascorbic acids. Other acids may be employed, but citric acid is most preferred. Examples of mineral acids which are water soluble and effective in this invention include hydrochloric acid and phosphoric acid. Any of combination of organic carboxylic acids and mineral acids can be used, the main requirement is that the final pH of the solution for administration is that the pH of said solution should be about 2.0 to 6.0 and preferably in the range of about 3.0 to about 5.0.

Yet another embodiment of the claimed invention is that the parenteral solution of HECPT contains from about 0.1 mg to about 5.0 mg activity of 7ethyl-10-hydroxy camptothecin per ml of the undiluted solution. Oral formulations can consist of a broader range and higher total HECPT concentrations as drug suspensions. Oral formulation solutions of HECPT can have a concentration of HECPT from about 0.1 mg to about 20 mg per milliliter of non-aqueous solution. These concentration ranges would be effective and useful for both oral and parenteral administration of the HECPT to human patients with cancer.

When oral dosages are to be administered in a capsule form, it is useful in many instances to have a more concentrated solution of HECPT suitable for encapsulation within a soft or hard gelatin capsule. Concentrated solutions allow the preparation of capsules of smaller size which allows easier ingestion by the patient, and may also reduce the number of capsules to be swallowed. These factors are important in view of the generally poor condition of cancer patients.

Taurocholic acid, a bile acid, may enhance in the intestinal absorption of the drug in certain patients. The present invention takes advantage of the discovery that taurocholic acid, or a pharmaceutically acceptable salt thereof, when included with HECPT in a solution dosage composition, results in improved absorption of the drug following ingestion of the composition. It is reported by some investigators that this is due to the formation of a micellar solution of HECPT on dilution thereof with the gastric contents. Applicants do not wish to be bound, however, by any claim of such a mechanism.

The phenomenon of micellar solubilization of poorly water-soluble drugs mediated by bile acids, including taurocholic acid, has been previously reported with respect to glutethimide, hexestrol, griseofulvin (Bates et al.), reserpine (Malone et al.) and fatty acids and cholesterol (Westergaard et al.). The use of taurocholic acid or a pharmaceutically acceptable salt thereof in the present invention involves a pharmaceutical solution of HECPT which has the unique property of providing a stable apparent solution of the drug upon dilution thereof with from 1 to 100 volumes of water.

The solution is stable and free of precipitate for a period of at least two hours; sufficient time to permit administration and absorption by the patient.

It has been observed with similar solutions of etoposide, a chemically unrelated poorly water soluble anticancer drug, that the bioavailability of the drug following oral administration is substantially equivalent to that achieved by intravenous administration of a solution of etoposide (U.S. Pat. No. 4,713,246). Analogous to that of etoposide, it is believed that ingestion of the present dosage form of HECPT and resulting dilution thereof by the stomach contents, results in the formation of a micellar solution of HECPT in the stomach which is readily absorbed by the gastrointestinal tract. Applicants do not wish to be bound, however, by any theoretical explanation of the mechanism by which the superior oral bioavailability of the present HECPT formulation is achieved.

Formulations Containing HECPT

A preferred embodiment of the claimed invention is a formulation containing 7ethyl-10-hydroxy camptothecin (HECPT) dissolved or suspended in dimethylisosorbide or dimethylacetamide containing from about 0.1 mg to about 5.0 mg 7ethyl-10-hydroxy camptothecin activity per 1 (one) ml of dimethylisosorbide or dimethylacetamide.

A preferred embodiment of the claimed invention is an antitumor composition comprising a solution of 7ethyl-10-hydroxy camptothecin dissolved in dimethylisosorbide or dimethylacetamide containing from about 0.1 mg to about 5.0 mg 7ethyl-10-hydroxy camptothecin activity per ml in a solution consisting of between about 500 and about 10,000 parts of dimethylisosorbide or dimethylacetamide by total solution weight and containing from about 1 to about 1,000 parts by weight of a pharmaceutically acceptable acid per ml of formulation. Inventors prefer to use about 50 to about 500 parts by weight of a pharmaceutically acceptable acid per parts by weight of the total solution.

Also embodied in this formulation wherein said carboxylic acid is selected from the group consisting of tartaric acid, citric acid, succinic, fumaric, maleic acid, gluconic acid, ascorbic acid, taurocholic acid, and taurocholic acid in an admixture with citric acid and wherein said carboxylic acid is selected from the group consisting of citric acid and taurocholic acid in an admixture with citric acid or wherein said mineral acid is selected from the group consisting of hydrochloric acid, and phosphoric acid. Yet another embodiment of this formulation is wherein said admixture of a carboxylic acid and a mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid. Also, the acid of this formulation is in an amount sufficient to result in a final pH of between about 2.0 and about 6.0 or is in an amount sufficient to result in a final pH of between about 3.0 and about 5.0.

An additional embodiment of the claimed subject matter is wherein said part by weight of a pharmaceutically acceptable acid is from about 1 to about 1,000 parts by weight of the total solution and the acid is selected from the following group, alone or in any combination: citric acid, hydrochloric acid and phosphoric acid.

Another embodiment of this invention is the formulation or an antitumor composition comprising a solution or suspension of about 0.1 to about 15.0 mg of 7ethyl-10-hydroxy camptothecin per 1 (one) ml of a formulation consisting of 500 to 10,000 parts by weight of dimethylisosorbide or dimethylacetamide by weight of the total formulation in the presence of a pharmaceutically acceptable acid and a glycol selected from the groups consisting of polyethylene glycol, propylene glycol, and a combination of a polyethylene glycol and propylene glycol.

Another aspect of this invention is this formulation or antitumor composition comprising a solution or suspension of about 0.1 to about 15.0 mg of 7ethyl-10-hydroxy camptothecin per 1 (one) ml of a formulation consisting of dimethylisosorbide or dimethylacetamide in the presence of a pharmaceutically acceptable acid, wherein said solution or suspension further comprises taurocholic acid or a pharmaceutically acceptable salt thereof, and a glycol selected from the group consisting of polyethylene glycol, propylene glycol, and a combination of a polyethylene glycol and propylene glycol.

Yet another aspect of this invention is a formulation or solution or suspension of antitumor composition having about 0.1 to about 15.0 mg of 7ethyl-10-hydroxy camptothecin per 1 (one) ml of a formulation containing 500 to 10,000 parts by weight dimethylisosorbide or dimethylacetamide based on the weight of the total formulation, between about 1 and about 1,000 parts by weight of a pharmaceutically acceptable acid, between about 10 and about 2,500 parts by weight of taurocholic acid or a pharmaceutically acceptable salt thereof, 20 to 8,000 parts by weight of a polyethylene glycol or propylene glycol per total solution weight. An additional embodiment is wherein said acid is an organic carboxylic acid and the inventors prefer citric acid.

Embodied in this invention is the formulation wherein said carboxylic acid is selected from the group consisting of tartaric acid, citric acid, succinic, fumaric, maleic acid, gluconic acid, ascorbic acid, taurocholic acid, and taurocholic acid in an admixture with citric acid. Also, this formulation is further defined wherein said carboxylic acid is selected from the group consisting of citric acid and taurocholic acid in an admixture with citric acid and wherein said mineral acid is selected from the group consisting of hydrochloric acid, and phosphoric acid. Also embodied, wherein said acid is an admixture of a carboxylic acid and a mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid and wherein said acid is in an amount sufficient to result in a final pH of between about 2.0 and about 6.0 or said acid is in an amount sufficient to result in a final pH of between about 3.0 and about 5.0.

Another aspect of this invention is the formulation or antitumor composition further comprises a lower alcohol. Many different alcohols would be effective in this invention, but the inventors prefer to use ethanol, benzyl alcohol or a combination of ethanol and benzyl alcohol. For this invention, ethanol, ethyl alcohol and dehydrated ethyl alcohol are used interchangeably. Another embodiment of the claimed invention is the formulation or antitumor composition further comprises glycerin as a co-solvent.

A further aspect of this invention is an oral 7-ethyl-10-hydroxy camptothecin formulation comprising 7-ethyl-10-hydroxy camptothecin, dimethylacetamide, a pharmaceutically acceptable acid selected from the group consisting of a carboxylic acid, mineral acid and a carboxylic acid in an admixture with a mineral acid, taurocholic acid or a pharmaceutically acceptable salt thereof, and a glycol selected from the group consisting of polyethylene glycol, propylene glycol and polyethylene glycol in an admixture with propylene glycol. This oral formulation has between about 0.1 and about 15.0 mg of 7-ethyl-10-hydroxy camptothecin per one ml of formulation having between about 500 and about 10,000 parts by weight dimethylacetamide based on the weight of the total formulation, between about 1 and about 1,000 parts by weight of said acid, between about 10 and about 2,500 parts by weight of taurocholic acid or a pharmaceutically acceptable salt thereof, and between about 20 and about 8,000 parts by weight of said glycol per total formulation weight. Also, this oral formulation further has between about 20 parts and about 7,000 parts of a lower alcohol selected from the group consisting of ethanol, benzyl alcohol, and ethanol in an admixture with benzyl alcohol and between about 1 part and about 1,000 parts of glycerin. And, the carboxylic acid in this oral formulation is selected from the group consisting of tartaric acid, citric acid, succinic, fumaric, maleic acid, gluconic acid, ascorbic acid, taurocholic acid, and taurocholic acid in an admixture with citric acid.

Yet another embodiment of this invention is an antitumor composition comprising a solution or suspension containing about 0.1 to about 15.0 mg of 7ethyl-10-hydroxy camptothecin per 1 (one) ml of a formulation containing 500 to 10,000 parts by weight of dimethylisosorbide or dimethylacetamide based on the weight of the total formulation in the presence of a pharmaceutically acceptable acid, wherein said solution further comprises taurocholic acid or a pharmaceutically acceptable salt thereof, a glycol selected from the group consisting of polyethylene glycol, propylene glycol, and a combination of both, ethanol, glycerin, and a buffer, such as sodium acetate, to maintain an acidic pH upon dilution with an aqueous vehicle of less than 6.0 and greater than 2.0.

An additional aspect of this invention is wherein said solution or suspension contains about 0.1 to about 15.0 mg of 7ethyl-10-hydroxy camptothecin per 1 (one) ml of a formulation containing 500 to 10,000 parts by weight of dimethylisosorbide or dimethylacetamide in based on the weight of the total formulation, 1 to 1,000 parts by weight of a pharmaceutically acceptable acid, 10 to 2,500 parts by weight of taurocholic acid or a pharmaceutically acceptable salt thereof, 20 to 8,000 parts by weight of a polyethylene glycol or propylene glycol or a combination of a polyethylene glycol and propylene glycol, 1 to 1,000 parts by weight of glycerin, 20 to 7,000 parts by weight of lower alcohol selected from the group consisting of ethanol, benzyl alcohol and a combination of both, 0.1 to 750 parts by weight of a buffer based on the weight of the total formulation.

This oral formulation is further defined wherein said carboxylic acid is selected from the group consisting of tartaric acid, citric acid, succinic, fumaric, maleic acid, gluconic acid, ascorbic acid, taurocholic acid, and taurocholic acid in an admixture with citric acid and wherein said acid is selected from the group consisting of citric acid and taurocholic acid in an admixture with citric acid. Also embodied in this invention is wherein said acid is taurocholic acid in an admixture with citric acid and wherein said mineral acid is selected from the group consisting of hydrochloric acid, and phosphoric acid. Further, the admixture of a carboxylic acid and a mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid.

Also, the acid is in an amount sufficient to result in a final pH of between about 2.0 and about 6.0 or the acid is in an amount sufficient to result in a final pH of between about 3.0 and about 5.0.

Another embodiment of this invention is wherein said polyethylene glycol has a molecular weight of about 300 to 400 and the antitumor composition further comprises a non-ionic surfactant. There are many different surfactants but the inventors prefer a poloxamer. The preferred poloxamer is poloxamer 127.

Yet another embodiment of this invention is a formulation or an antitumor composition comprising a solution or suspension of about 0.1 to about 15.0 mg of 7-ethyl-10-hydroxy camptothecin per 1 (one) ml of a formulation consisting of 500 to 10,000 parts by weight of dimethylisosorbide or dimethylacetamide based on the weight of the total formulation in the presence of a pharmaceutically acceptable acid, wherein said solution further comprises a lower alcohol and a glycol selected from the group consisting of polyethylene glycol, a propylene glycol, and a combination of a polyethylene glycol and propylene glycol.

Yet another embodiment of this invention is a formulation or an antitumor composition comprising a solution or suspension of about 0.1 to about 15.0 mg of 7-ethyl-10-hydroxy camptothecin per 1 (one) ml of a formulation consisting of 500 to 10,000 parts by weight of dimethylisosorbide or dimethylacetamide based on the weight of the total formulation in the presence of a pharmaceutically acceptable acid, wherein said solution further comprises a lower alcohol, polyethylene glycol or propylene glycol, or a combination of a polyethylene glycol and propylene glycol, and surfactant.

As a more preferred embodiment for this antitumor composition, the pharmaceutically acceptable organic acid is citric acid, the polyethylene glycol is PEG 300, the lower alcohol is ethanol and the surfactant is polysorbate-80.

An aspect of this invention is an oral 7-ethyl-10-hydroxy camptothecin formulation comprising 7-ethyl-10-hydroxy camptothecin, dimethylacetamide, a pharmaceutically acceptable acid selected from the group consisting of a carboxylic acid, mineral acid and a carboxylic acid in an admixture with a mineral acid, taurocholic acid or a pharmaceutically acceptable salt thereof, and a glycol selected from the group consisting of polyethylene glycol, propylene glycol and polyethylene glycol in an admixture with propylene glycol, ethanol, glycerin, and a buffer to maintain an acidic pH in a range between about 2.0 and 6.0 upon dilution with an aqueous vehicle, wherein said oral formulation has between about 0.1 and about 15.0 mg of 7-ethyl-10-hydroxy camptothecin per one ml of formulation having between about 500 and about 10,000 parts by weight of dimethylacetamide based on the weight of the total formulation. This formulation has between about 1 part and about 1,000 parts by weight of said pharmaceutically acceptable acid, between about 10 parts and about 2,500 parts by weight of taurocholic acid or a pharmaceutically acceptable salt thereof, between about 20 parts and about 8,000 parts by weight of said glycol, between about 1 part and about 1,000 parts by weight of glycerin, between about 20 parts and about 7,000 parts by weight of ethanol, between about 0.1 part and about 750 parts by weight of a buffer based on the weight of the total formulation and wherein said buffer is sodium acetate. Also, the glycol in this oral formulation is selected from the group consisting of polyethylene glycol 300 and polyethylene glycol 400 and this oral formulation further has a surfactant wherein said surfactant is poloxamer and more specifically wherein said poloxamer is poloxamer 127.

Further, in this oral formulation wherein said carboxylic acid is selected from the group consisting of tartaric acid, citric acid, succinic, fumaric, maleic acid, gluconic acid, ascorbic acid, taurocholic acid, and taurocholic acid in an admixture with citric acid. Also, this oral formulation wherein said carboxylic acid is selected from the group consisting of citric acid and taurocholic acid in an admixture with citric acid and wherein said carboxylic acid is citric acid and wherein said mineral acid is selected from the group consisting of hydrochloric acid, and phosphoric acid and wherein said admixture of a carboxylic acid and a mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid. Also, this oral formulation wherein said acid is in an amount sufficient to result in a final pH of between about 2.0 and about 6.0 or more specifically, said acid is in an amount sufficient to result in a final pH of between about 3.0 and about 5.0.

Another aspect of this invention is a formulation or an antitumor composition comprising a solution or suspension of about 0.1 mg to about 15.0 mg of 7ethyl-10-hydroxy camptothecin per 1 (one) ml of a formulation consisting of 500 to 10,000 parts by weight of dimethylisosorbide or dimethylacetamide based on the weight of the total formulation in the presence of about 1 to 1,000 parts by weight of a pharmaceutically acceptable acid. This antitumor composition further contains about 20 to about 8,000 parts by weight of a polyethylene glycol or polypropylene glycol or a combination of a polyethylene glycol and propylene glycol, about 20 to about 7,000 parts by weight of a pharmaceutically acceptable alcohol, and about 20 to about 8,000 parts by weight of a non-ionic surfactant based on the total weight of the formulation.

More preferred for this antitumor composition is when the acid is citric acid, the polyethylene glycol is PEG 300, the alcohol is ethanol or a combination of ethanol and benzyl alcohol and the surfactant is polysorbate-80.

Another aspect of this invention is an antitumor composition comprising a solution or suspension about 0.1 mg to about 15.0 mg of 7ethyl-10 hydroxy camptothecin per 1 (one) ml of formulation containing about 500 to about 10,000 parts by weight of dimethylisosorbide or dimethylacetamide based on the weight of the total formulation in the presence of 1 to 1,000 parts by weight of a pharmaceutically acceptable organic carboxylic acid. This formulation further contains about 20 to about 7,000 parts by weight of a pharmaceutically acceptable alcohol and about 20 to about 8,000 parts by weight of a non-ionic surfactant.

More specifically for this antitumor composition, the acid is citric acid, the alcohol is ethanol, and the non-ionic surfactant is comprised of polyoxyethylated castor oil.

Another embodiment of this invention is an antitumor composition comprising a solution or suspension of 0.1 mg to about 15.0 mg of 7ethyl-10-hydroxy camptothecin per 1 (one) ml of formulation containing 500 to 10,000 parts by weight of dimethylisosorbide or dimethylacetamide based on the total weight of the formulation further contains about 20 to about 8,000 parts by weight of polyoxyethylated castor oil, about 20 to about 7,000 parts by weight of ethyl alcohol, and 1 to about 1,000 parts by weight of citric acid based on the total weight of the formulation.

In a more preferred embodiment, HECPT is solubilized in a manner suitable for parenteral clinical use by forming a nonaqueous solution of about 0.1 to about 1.0 mg of HECPT dissolved in 1 (one) ml of a formulation consisting of 500 to 10,000 parts by weight of dimethylacetamide based on the total weight of the formulation, ethyl alcohol 20 to 7,000 parts by weight of formulation, benzyl alcohol 20 to 4,000 parts by weight, citric acid 1 to 1,000 parts by weight, a polyethylene glycol (PEG 300 or PEG 400) 20 to 8,000 parts by weight, polysorbate-80 (Tween 80) 20 to 8,000 parts by weight based on the total weight of the formulation with a pH of 3 to 5.

Another preferred parenteral formulation comprises HECPT formulated for aqueous dilution prior to parenteral administration made of 0.01 to about 1.0 mg HECPT per ml of a formulation containing 20 to 8,000 parts by weight of Cremaphor EL (polyoxyethylated castor oil), 20 to 7,000 parts by weight ethyl alcohol, dimethyacetamide 500 to 10,000 parts by weight, and citric acid 1 to 1,000 parts by weight based on the total weight of the formulation.

Another aspect of this invention is a 7-ethyl-10-hydroxy camptothecin formulation comprising 7-ethyl-10-hydroxy camptothecin, dimethylacetamide, a pharmaceutically acceptable acid selected from the group consisting of a carboxylic acid, mineral acid and a carboxylic acid in an admixture with a mineral acid, a glycol selected from the group consisting of polyethylene glycol, propylene glycol and polyethylene glycol in an admixture with propylene glycol, and a lower alcohol selected from the group consisting of ethanol, benzyl alcohol, and ethanol in an admixture with benzyl alcohol. This formulation can be used for both oral and parenteral administration.

Another embodiment of this invention is the formulation has between about 0.1 and about 15.0 mg of 7ethyl-10-hydroxy camptothecin per one ml of formulation having between about 500 parts and about 10,000 parts by weight of dimethylacetamide based on the weight of the total formulation, between about 1 part and about 1,000 parts by weight of said acid, between about 20 parts and about 7,000 parts by weight of said lower alcohol, and between about 20 parts and about 8,000 parts by weight of said glycol. Also embodied in this invention wherein said carboxylic acid is selected from the group consisting of tartaric acid, citric acid, succinic, fumaric, maleic acid, gluconic acid, ascorbic acid, taurocholic acid, and taurocholic acid in an admixture with citric acid and wherein said carboxylic acid is selected from the group consisting of citric acid and taurocholic acid in an admixture with citric acid. Also, wherein said carboxylic acid is citric acid and wherein said mineral acid is selected from the group consisting of hydrochloric acid, and phosphoric acid or wherein said admixture of a carboxylic acid and a mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid. Another embodiment is wherein said acid is in an amount sufficient to result in a final pH of between about 2.0 and about 6.0 and more specifically wherein said acid is in an amount sufficient to result in a final pH of between about 3.0 and about 5.0.

Another aspect of this invention is a 7-ethyl-10-hydroxy camptothecin formulation comprising 7-ethyl-10-hydroxy camptothecin, dimethylacetamide, a pharmaceutically acceptable acid selected from the group consisting of a carboxylic acid, mineral acid and a carboxylic acid in an admixture with a mineral acid, a glycol selected from the group consisting of polyethylene glycol, propylene glycol and polyethylene glycol in an admixture with propylene glycol, a lower alcohol selected from the group consisting of ethanol, benzyl alcohol, and ethanol in an admixture with benzyl alcohol and a surfactant. Also, this formulation has between about 0.1 and about 15.0 mg of 7ethyl-10-hydroxy camptothecin per one ml of formulation having between about 500 parts and about 10,000 parts by weight of dimethylacetamide based on the weight of the total formulation, between about 1 part and about 1,000 parts by weight of said acid, between about 20 parts and about 7,000 parts by weight of said lower alcohol, between about 20 parts and about 8,000 parts by weight of said glycol, and between about 0.1 part and about 800 parts by weight of said surfactant. And, wherein said acid is citric acid, said glycol is polyethylene glycol 300, said lower alcohol is ethanol and said surfactant is polysorbate-80 and wherein said carboxylic acid is selected from the group consisting of tartaric acid, citric acid, succinic, fumaric, maleic acid, gluconic acid, ascorbic acid, taurocholic acid, and taurocholic acid in an admixture with citric acid. Further, wherein said carboxylic acid is selected from the group consisting of citric acid and taurocholic acid in an admixture with citric acid and wherein said carboxylic acid is citric acid. Also, the acid for this formulation wherein said mineral acid is selected from the group consisting of hydrochloric acid, and phosphoric acid or wherein said admixture of a carboxylic acid and a mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid. The acid of this formulation further wherein said acid is in an amount sufficient to result in a final pH of between about 2.0 and about 6.0 and more specifically, wherein said acid is in an amount sufficient to result in a final pH of between about 3.0 and about 5.0.

Yet another aspect of this invention is a 7-ethyl-10-hydroxy camptothecin formulation comprising 7-ethyl-10-hydroxy camptothecin, dimethylacetamide, a pharmaceutically acceptable acid selected from the group consisting of a carboxylic acid, mineral acid and a carboxylic acid in an admixture with a mineral acid, a glycol selected from the group consisting of polyethylene glycol, propylene glycol and polyethylene glycol in an admixture with propylene glycol, a lower alcohol selected from the group consisting of ethanol, benzyl alcohol, and ethanol in an admixture with benzyl alcohol and a surfactant. This formulation may be administered to a patient with cancer either orally or parenterally. Also, this formulation has between about 0.1 and about 15.0 mg of 7ethyl-10-hydroxy camptothecin per one ml of formulation having between about 500 parts and about 10,000 parts by weight of dimethylacetamide based on the weight of the total formulation, between about 1 part and about 1,000 parts by weight of said acid, between about 20 parts and about 7,000 parts by weight of said lower alcohol, between about 20 parts and about 8,000 parts by weight of said glycol, and between about 20 parts and about 8,000 parts by weight of said surfactant based on the total weight of the formulation.

The acid of this formulation wherein said acid is citric acid, said glycol is polyethylene glycol 300, said lower alcohol is ethanol and said surfactant is polysorbate-80 and wherein said carboxylic acid is selected from the group consisting of tartaric acid, citric acid, succinic, fumaric, maleic acid, gluconic acid, ascorbic acid, taurocholic acid, and taurocholic acid in an admixture with citric acid. Also, wherein said carboxylic acid is selected from the group consisting of citric acid and taurocholic acid in an admixture with citric acid. Further wherein said carboxylic acid is citric acid and wherein said mineral acid is selected from the group consisting of hydrochloric acid, and phosphoric acid or wherein said admixture of a carboxylic acid and a mineral acid is selected from the group consisting of hydrochloric acid in an admixture with taurocholic acid, phosphoric acid in an admixture with taurocholic acid, citric acid in an admixture with phosphoric acid and citric acid in an admixture with hydrochloric acid. The acid in this formulation wherein said acid is in an amount sufficient to result in a final pH of between about 2.0 and about 6.0 and more specifically, wherein said acid is in an amount sufficient to result in a final pH of between about 3.0 and about 5.0.

Another aspect of this invention is a 7-ethyl-10-hydroxy camptothecin formulation comprising 7-ethyl-10-hydroxy camptothecin, dimethylacetamide, and a pharmaceutically acceptable carboxylic acid having between about 0.1 and about 15.0 mg of 7ethyl-10-hydroxy camptothecin per one ml of formulation having between about 500 parts and about 10,000 parts by weight of dimethylacetamide based on the weight of the total formulation, and between about 1 part and about 1,000 parts by weight of said carboxylic acid. This formulation further has a lower alcohol selected from the group consisting of ethanol, benzyl alcohol, and ethanol in an admixture with benzyl alcohol and a surfactant wherein said formulation contains between about 20 parts and about 7,000 parts by weight of said lower alcohol and between about 20 parts and about 8,000 parts by weight of said surfactant based on the total weight of the formulation. This formulation wherein said carboxylic acid is selected from the group consisting of tartaric acid, citric acid, succinic, fumaric, maleic acid, gluconic acid, ascorbic acid, taurocholic acid, and taurocholic acid in an admixture with citric acid and wherein said carboxylic acid is selected from the group consisting of citric acid and taurocholic acid in an admixture with citric acid. Further, wherein said carboxylic acid is citric acid and wherein said acid is in an amount sufficient to result in a final pH of between about 2.0 and about 6.0 and more specifically, wherein said acid is in an amount sufficient to result in a final pH of between about 3.0 and about 5.0. The acid in this formulation wherein said acid is citric acid, said lower alcohol is ethanol and said surfactant is polyoxyethylated castor oil.

Yet another aspect of this invention is a 7-ethyl-10-hydroxy camptothecin formulation comprising between about 0.1 mg and about 15.0 mg of 10-hydroxy 7-ethyl camptothecin per one ml of formulation having between about 500 parts and about 10,000 parts by weight of dimethylacetamide based on the total weight of the formulation, between about 20 parts and about 8,000 parts by weight of polyoxyethylated castor oil, between about 20 parts and about 7,000 parts by weight of ethyl alcohol, and between about 1 part and about 1,000 parts by weight of citric acid based on the total weight of the formulation. This formulation may be orally or parenterally administered to a patient with cancer.

Another aspect is a 7-ethyl-10-hydroxy camptothecin formulation comprising between about 0.1 and about 15.0 mg of 7-ethyl-10-hydroxy camptothecin in one ml of a formulation having between about 500 parts and about 10,000 parts by weight dimethylacetamide based on the total weight of the formulation, between about 20 parts and about 7,000 parts by weight of formulation of ethyl alcohol, between about 20 parts and about 4,000 parts by weight of benzyl alcohol, between about 1 part and about 1,000 parts by weight citric acid, between about 20 parts and about 8,000 parts by weight of a glycol selected from the group consisting of polyethylene glycol 300, polyethylene glycol 400, propylene glycol, polyethylene glycol 300 in an admixture with propylene glycol and polyethylene glycol 400 in an admixture with propylene glycol, and between about 20 parts and about 8,000 parts by weight of a surfactant selected from the group consisting of polysorbate-80 and Tween 80 based on the total weight of the formulation. This formulation is represented in the tables. Also the acid in this formulation wherein said acid is in an amount sufficient to result in a final pH of between about 2.0 and about 6.0 and more specifically, wherein said acid is in an amount sufficient to result in a final pH of between about 3.0 and about 5.0.

Another aspect of this invention is an oral 7-ethyl-10-hydroxy camptothecin formulation comprising between about 0.1 and about 15.0 mg of 7-ethyl-10-hydroxy camptothecin in one ml of a formulation having between 500 to 10,000 parts by weight dimethylacetamide based on the total weight of the formulation, between about 20 parts and about 7,000 parts by weight of formulation of ethyl alcohol, between about 1 part and about 1,000 parts by weight citric acid and between about 20 parts and about 8,000 parts by weight of Cremaphor EL (polyoxyethylated castor oil) based on the total weight of the formulation. For this invention, Cremaphor EL and polyoxyethylated castor oil are used interchangeably.

Yet another aspect of this invention is an oral 7-ethyl-10-hydroxy camptothecin formulation having between about 0.1 mg and about 15.0 mg of 7-ethyl-10-hydroxy camptothecin per ml of formulation in parts by weight per one ml of formulation having between about 500 parts and about 10,000 parts by weight of dimethylacetamide, between about 1 part and about 1,000 parts by weight citric acid, between about 1 part and about 1000 parts by weight glycerin, between about 20 parts and about 8,000 parts by weight of a glycol selected from the group consisting of polyethylene glycol 300 and polyethylene glycol 400, between about 20 parts and about 7,000 parts by weight ethyl alcohol, between about 0.1 part and about 250 parts by weight sodium acetate, and between about 0.1 part and about 800 parts by weight of a surfactant based on the weight of the total formulation. This oral formulation further having between about 10 parts and about 2,500 parts by weight of taurocholic acid or a pharmaceutically acceptable salt thereof based on the weight of the total formulation weight. The surfactant of this oral formulation wherein said surfactant is pluronic F-127 poloxamer.

This invention also embodies the formulation of claims 22, 31, 39, 49, 62, 71, 81, 91, 100, 101, 104, 105, 111, and 112 wherein said formulation is sterilized and prepared for oral, intrapleural, intrathecal, intracisternal, intravesicular, intraperitoneal, topical or parenteral administration to a patient with cancer.

Also, the oral formulation of claims 22, 31, 39, 49, 62, 71, 81, 100, 101, 104, and 105 wherein said formulation is encapsulated within a hard gelatin capsule and wherein the oral formulation of claims 22, 31, 39, 49, 62, 71, 81, 100, 101, 104, and 105 wherein said formulation is encapsulated within a soft gelatin capsule. Oral formulation soft and/or hard gelatin capsules may be composed of any of a number of different compounds used for this purpose including, for example, a mixture of gelatin, glycerin, sorbitol, purifiers, purified water, and parabens. For this invention, oral formulations may or may not include taurocholic acid and if the formulation does include taurocholic acid, then it is administered orally.

Another aspect of this invention is a 7ethyl-10-hydroxy camptothecin formulation comprising 7ethyl-10-hydroxy camptothecin and dimethylisosorbide.

Also an aspect of this invention is a 7ethyl-10-hydroxy camptothecin formulation comprising 7ethyl-10-hydroxy camptothecin, dimethylisosorbide, and a pharmaceutically acceptable acid selected from the group consisting of a carboxylic acid, a mineral acid and an admixture of a carboxylic acid and a mineral acid. Further, the acid in this formulation wherein said acid is in an amount sufficient to result in a final pH of between about 2.0 and about 6.0 and more specifically, wherein said acid is in an amount sufficient to result in a final pH of between about 3.0 and about 5.0.

Oral Formulations of HECPT

Yet another embodiment of this invention for oral administration to a patient with cancer is the HECPT dissolved in dimethylisosorbide (DMI) in the presence of a pharmaceutically acceptable acid or the HECPT is dissolved in dimethylacetamide (DMA) in the presence of a pharmaceutically acceptable acid.

A further embodiment of this invention is the claimed composition and method of administering the composition by encapsulating the claimed formulations within a hard gelatin capsule. Yet another embodiment of the claimed composition and method of administering the composition is encapsulating the claimed formulations within a soft gelatin capsule. One of ordinary skill in the art will know that any of the claimed formulations adapted for oral administration can be used as the fill for the soft or hard gelatin capsule.

A more specific embodiment of the claimed invention is an oral formulation of HECPT in soft gelatin capsules (comprised of gelatin, glycerin, sorbitol, purifiers, purified water) containing about 0.1 mg to about 15.0 mg of HECPT per ml of formulation containing in parts by weight per 1 (one) ml of formulation, citric acid 1 to 1,000 parts by weight, glycerin 1 to 1000 parts by weight, polyethylene glycol (PEG 300 or PEG 400) 20 to about 1,000 parts by weight of formulation, ethyl alcohol 20 to about 7,000 parts by weight, sodium acetate 0.1 to 250 parts by weight, a surfactant 0.1 to 800 parts by weight, and 500 to 10,000 parts by weight of dimethylacetamide based on the weight of the total formulation. A more preferred oral formulation will include as a surfactant pluronic F-127 poloxamer.

Another preferred oral formulation will include the addition of taurocholic acid or a pharmaceutically acceptable salt thereof of about 10 to 2,500 parts by weight of total formulation weight. The soft or hard gelatin capsules may also be composed of any of a number of compounds used for this purpose including, for example, a mixture of gelatin, glycerin, sorbitol, purified water, and parabens.

Table 1 below indicates parts by weight of different components to be included in the oral formulation to be administered in capsules. Four components are marked with an "**" which denotes that the components are "optional." For the purpose of this invention, inclusion of these components depends on a variety of different factors; i.e. the specific type of cancer the patient has, treated previously and other medical conditions which may influence the selection of certain therapies.

TABLE 1

| Ingredients | Parts by Weight |
|---|---|
| 7- ethyl- 10 - hydroxy Camptothecin | 0.1 to 15.0 mg/ml |
| Acid Selected from the group of citric, hydrochloric, or phosphoric | 1 to 1,000 |
| Glycerin ** | 1 to 1,000 |

TABLE 1-continued

| Ingredients | Parts by Weight |
| --- | --- |
| PEG 300 | 20 to 8,000 |
| PEG 400 | |
| Propylene glycol | |
| EtOH ** | 20 to 7,000 |
| Dimethylacetamide | 500 to 10,000 |
| or | |
| Dimethylisosorbide | |
| Poloxamer surfactant (Pluronic F-127) ** | 0.1 to 800 |
| Sodium Acetate ** | 0.1 to 250 |
| Taurocholic Acid ** | 10 to 2,500 |

Clinicians will administer HECPT to human patients with cancer according to doses and schedules that maximize its potential antitumor effects and diminish its potential toxic side effects. Except at extremely high doses which produce high plasma concentrations of the drug, the antitumor activity of HECPT can be greatly increased by increasing the duration of exposure (time dependent) relative to antitumor effects achieved by increasing the dose (dose dependent) of the drug. The greater antitumor effects associated with increasing the duration of exposure is a finding that is most likely related to the predominant S-phase mode of antitumor activity of CPT-11 and HECPT. HECPT is an S-phase-active agent; therefore, the greatest antitumor effect in humans will likely be observed with prolonged infusion or closely spaced repetitive administration schedules. Such schedules of administration would expose more cycling tumor cells to the drug and increase the frequency of exposure of the tumor cells in S-phase to sufficiently toxic levels of the drug.

Initially, patients may be treated in a dose escalation protocol to determine the maximal tolerated dose of the HECPT formulation. In determining a safe starting dose for HECPT, the data from Tables 2 and 3 are helpful. For the purpose of this invention, "AUC" is defined as "area under the curve" and "CpMax" is defined as "the maximum plasma concentrate at the end of I.V. infusion."

TABLE 3

Fractional Amounts of Lactone Species of CPT-11 and HECPT as Function of Increasing Single Dose I.V. From Rothenberg et. al.

| Dose | CPT-11 AUC Based | HECPT AUC Based | CPT-11 CpMax Based | HECPT CpMax Based |
| --- | --- | --- | --- | --- |
| 50 mg/m$^2$ | 0.41 | 0.29 | 0.51 | 0.50 |
| 80 mg/m$^2$ | 0.30 | 0.50 | 0.44 | 0.39 |
| 100 mg/m$^2$ | 0.33 | 0.58 | 0.53 | 0.45 |
| 125 mg/m$^2$ | 0.39 | 0.43 | 0.55 | 0.41 |
| 150 mg/m$^2$ | 0.33 | 0.30 | 0.42 | 0.36 |
| 180 mg/m$^2$ | 0.33 | 0.63 | 0.42 | 0.45 |

Data obtained using the continuous infusion schedule of Ohe et al. shows that the ratio CPT-11 to HECPT AUCs increases gradually as a function of dose and that this increase is substantially more marked in a single dose study. The data in Table 2 supports the conclusion that conversion of CPT-11 to HECPT is a saturable process which is variable among patients, and that increases in the dose (e.g., above 30 mg/m$^2$/d) of CPT-11 can result in a decrease in the CpMax of HECPT using a 5 day continuous infusion schedule. Although the factors involved in interpatient variability is not completely understood, some variability in the pharmacology and metabolic conversion of CPT-11 to HECPT probably exists based on the pharmacologic data reported from several investigators. This variability in the conversion of CPT-11 to HECPT is likely to be a result in instances of unexpected toxicity or lack of clinical effect by the use of CPT-11. In Table 3, the overall fractional concentration of the lactone species of CPT-11 and HECPT appear to remain fairly constant through a range of doses.

The administration of HECPT may be carried out using various schedules and dosages. For example:

1. For intravenous administration, a suitable dose range is about 0.5 mg to 5.0 mg/m$^2$ per day using a 3 to 5 day continuous infusion schedule every 21 to 30 days or about 3.0 to about 30 mg/m$^2$ given as a 30 to 90 minute infusion every 21 to 30 days.

TABLE 2

Analysis of AUC and CpMax Ratios of CPT-11:HECPT

| | AUC CPT-11 (ug × hr/ml) | AUC HECPT (ug × hr/ml) | Ratio AUC CPT-11/HECPT | CpMax CPT-11:HECPT (ug/ml) | CpMax Ratio CPT 11:HECPT |
| --- | --- | --- | --- | --- | --- |
| Ohe et al. | | | | | |
| 25 mg/m$^2$/d × 5 | 14.1 | 1.08 | 13.0 | 1.178:0.0104 | 11.3:1 |
| 30 mg/m$^2$/d × 5 | 20.5 | 0.96 | 21.3 | 1.500:0.0105 | 14.2:1 |
| 35 mg/m$^2$/d × 5 | 20.5 | 0.91 | 22.5 | 1.538:0.0068 | 22.6:1 |
| 40 mg/m$^2$/d × 5 | 28.5 | 0.86 | 33.1 | 2.043:0.0080 | 25.5:1 |
| Rothenberg et al. | | | | | |
| 50 mg/m$^2$/wk × 4 | 1.13 | 0.0622 | 18.1 | 0.89:0.0264 | 33.7:1 |
| 100 mg/m$^2$/wk × 4 | 2.23 | 0.2148 | 10.4 | 1.29:0.0316 | 98.0:1 |
| 125 mg/m$^2$/wk × 4 | 2.97 | 0.1955 | 15.2 | 1.70:0.0393 | 43.2:1 |
| 150 mg/m$^2$/wk × 4 | 2.81 | 0.1232 | 22.8 | 1.56:0.0367 | 42.5:1 |
| 180 mg/m$^2$/wk × 4 | 3.83 | 0.2328 | 16.5 | 1.97:0.0262 | 75.2:1 |

2. Another schedule involves the administration of about 1.0 to 20.0 mg/m$^2$ daily for three consecutive days over 90 minutes intravenously every 21 to 28 days.
3. A suitable oral dose of the drug is about 0.5 to about 50 mg/m$^2$ per day for a period of 3 to 5 days and using divided dosages of administration of two to four times per day every 21 to 28 days.

The parenteral and oral doses can be administered under the supervision of a physician based on gradual escalation of the dosage to achieve the maximum tolerated dose in the individual patient. The oral administration schedule of HECPT may involve multiple daily doses or single daily doses for one or more consecutive days with the ability of the physician to optimize therapy by reaching the maximum effective antitumor dose that has the least toxicity in the individual patient.

In addition, patients may be given the lactone stable HECPT as an inpatient or outpatient using the following exemplary schedules:

1) 2.0 to 35 mg/m$^2$ given over 90 minutes I.V. every 21 to 28 days;
2) 1.0 to 15 mg/m$^2$ given daily for three consecutive days over 90 minutes I.V. every 21 to 28 days;
3) 1.0 to 20.0 mg/m$^2$ week given once per week×3 consecutive weeks over 90 minutes I.V. with 2 weeks rest after each 3 week cycle for pretreated patients;
4) 2.0 to 25 mg/m$^2$ given once per week×3 consecutive weeks over 90 minutes I.V. for previously untreated patients with 2 weeks rest after each 3 week cycle; and
5) 0.5 to 5.0 mg/m$^2$/d×3 to 5 consecutive days as a continuous I.V. infusion every 21 to 28 days.

In a preferred embodiment, HECPT is initially given at a lower dose. The dose of HECPT is then escalated at each successive cycle of treatment until the patient develops side effects which demonstrates individual therapeutic tolerance. The purpose of dose escalation is to safely increases the drug levels to a maximum tolerated dose and should result in increased cytotoxicity and improved antitumor activity.

Dosages can be escalated based on patient tolerance as long as unacceptable toxicity is not observed. "Unacceptable toxicity" is defined by World Health Organization (WHO) as grade 3 non-hematologic toxicity excluding nausea and vomiting and grade 4 vomiting or hematologic toxicity according to the National Cancer Institute common toxicity criteria. Since some clinical drug toxicity is anticipated in routine clinical oncology practice, appropriate treatment will be used to prevent toxicity (e.g., nausea and vomiting) or ameliorate signs and symptoms if they are observed (e.g., diarrhea). For example, antiemetics will be administered for nausea and vomiting, antidiarrheals for diarrhea, and antipyretics for fever. Appropriate dosages of steroids/antihistamines will also be used to prevent or ameliorate any anaphylactoid toxicity if an anaphylactoid reaction is observed.

Kaneda's HPLC method and further modifications by Barilero et al. are useful for the measuring quantities of HECPT in plasma and tissue. In these assays, plasma, serum, and tissue homogenate samples containing HECPT are immediately diluted 10-fold with 0.1N HCL to give final concentrations of about 100 ng/ml for HECPT. The diluted plasma or serum samples are applied to a C18 cassette of an automated sample processor (Analytichem International, Harbor City, Calif.), which is activated with 1.5 ml of methanol and water. The HPLC apparatus (Model LC-4A; Shimadzu Seisakusho) is linked to the automated sample processor, and a C18 reversed-phase column (LiChrosorb RP-18; 25×0.4 cm; Merck) with an RP-18 precolumn is used for chromatography. The mobile phases consists of CH$_3$CN/water (1/4,v/v) for HECPT. The flow rate and column temperature are 2.0 ml/min and 60 degrees Celsius for HECPT. A fluoro-spectromonitor (Model RF-530; Shimadzu Seisakusho) is set at an excitation wavelength of 373 nm and an emission wavelength of 380 nm and a wavelength of 540 nm for HECPT. The peak area is integrated by a data processor (Model C-R1BS Chromatopac; Shimadzu Seisakusho). HECPT gives retention times of 13.8 min. Calibration curves are established for each determination by 10% mouse serum in 0.1N HCL containing HECPT. Validations of HECPT determinations will be made by running samples versus real standards. The limit of determination is about 1 to 5 ng for HECPT using this assay.

A further embodiment of this invention is that the claimed formulations of HECPT dissolved or suspended in DMI or dissolved or suspended in DMA can be used in a variety of different cancer types. The claimed formulations and compositions of the invention may be used in treatment of a number of tumors including, without limitation, human cancers of the lung, breast, colon, prostate, melanoma, pancreas, stomach, liver, brain, kidney, uterus, cervix, ovaries, and urinary tract.

The site and type of tumor to be treated will, in many cases, influence the preferred route of administration and therapeutic regimen to be applied. Consequently, although the formulations of the invention may be most usually administered by intravenous injection or infusion, they also can be delivered directly into the tumor site or by other methods designed to target the drug directly to the tumor site. For example, in patients with malignant pleural effusion, the intrapleural route may be preferred; in patients with poor venous access the subcutaneous route of administration may be preferred; in patients with primary or metastatic cancer involving the brain or nervous system, the intracisternal or intrathecal route of administration may be most advantageous; in patients with malignant ascites secondary to cancer, one may select intraperitoneal administration; and in patients with bladder cancer direct intravesicular instillation may be most advantageous. Similarly, in tumors of the skin, the formulation may be topically applied. An oral formulation is also provided for use where suitable.

Thus, an additional aspect of this invention is an HECPT formulation or solution comprising HECPT dissolved in DMI or DMA, in the presence of a pharmaceutically acceptable acid and this solution is sterilized and prepared for oral, intrapleural, intrathecal, subcutaneous, intracisternal, intravesicular, intraperitoneal, topical or parenteral administration to a patient with cancer; thus this formulation is an antitumor composition.

A further aspect of this invention is that HECPT is a method of treatment of cancer in humans with convergent therapy or combination drug therapy. This method uses 7-ethyl-10-hydroxy camptothecin dissolved in dimethylisosorbide (DMI) or dimethylacetamide in (DMA), in the presence of pharmaceutically acceptable acid and co-administers it with additional drugs selected from the group consisting of, but not limited to, carmustine, azathioprine, cis-platinum, carboplatin, iproplatin, cyclophosphamide, ifosfamide, etoposide, ara-C, doxorubicin, daunorubicin, nitrogen mustard, 5-fluorouracil, bleomycin, mitomycin-C, fluoxymesterone, mechlorethamine, teniposide, hexamethylmelamine, leucovorin, melphelan, methotrexate, mercaptopurine, mitoxantrone, BCNU, CCNU, procarbazine, vincristine, vinblastine, vindesine, thioTEPA, amsacrine, G-CSF, GM-CSF, erythropoietin, γ-methylene-10-deazaaminopterin or γ-methylene-10-ethyl-10-deazaaminopterin, taxol, and 5-azacytidine. For the purpose of this invention, the terms convergent, co-administered, and combination are used interchangeably.

HECPT in DMI or DMA when administered parenterally, can be diluted with an appropriate volume of a parenteral vehicle to a concentration of about 0.1 mg/ml or a lower concentration of HECPT activity. A further embodiment of the claimed invention is a sterile solution of any of the claimed HECPT compositions and formulations for sterile administration to a patient with cancer upon dilution with a sterile parenteral vehicle. For the purposes of this invention, parenteral vehicles include dextrose 5 to 10% in water, 0.9% NaCl in water with or without 5% or 10% Dextrose, 0.45% NaCl in water with or without 5% or 10% Dextrose, and 3% NaCl in water with or without 5% to 10% Dextrose, or sterile lipid formulations, such as intralipid, used for parenteral nutritional support for cancer patients.

DETAILED DESCRIPTION OF PREFERRED EMBODIMENTS

In its preferred embodiments, this invention involves preparation and administration of novel lactone stable HECPT formulations as described below.

EXAMPLES

The following examples illustrate selected modes for carrying out the claimed invention and are not to be construed as limiting the specification and claims in any way.

The foregoing description of the formulation invention has been directed to particular preferred embodiments in accordance with the requirements of the patent statutes and for purposes of explanation and illustration. Those skilled in the art will recognize that many modifications and changes may be made without departing from the scope and the spirit of the invention.

Example 1

Formulation #1 of HECPT and DMI

For injection or infusion into aqueous body fluids, a formulation containing about 0.1 to about 2.5 mg of HECPT dissolved in 500 to 10,000 parts by weight of dimethylisosorbide based on the total weight of the formulation, about 1 to 1,000 parts by weight of a pharmaceutically acceptable acid, about 20 to 7,000 parts by weight of a pharmaceutically acceptable alcohol, about 20 to about 8,000 parts by weight a polyethylene glycol, and about 20 to about 8,000 parts of a non-ionic surfactant. Suitable alcohols include ethyl alcohol and benzyl alcohol. Suitable polyether glycols for this formulation include polyethylene glycol 300, polyethylene glycol 400 and propylene glycol. Suitable non-ionic surfactants include polysorbate-80. In a preferred embodiment, the formulation of HECPT is supplied as an intravenous injectable in a unit dose sealed vial comprising a sterile, non-aqueous solution of drug in a vehicle comprising dimethylisosorbide, ethyl alcohol with or without benzyl alcohol, citric acid, polyethylene glycol 300, and polysorbate (Tween 80) in acidified medium with a pH of 3 to 4 at a final concentration of 0.1 to 1.0 mg of HECPT per 1 ml of formulation.

Example 2

Formulation #2 of HECPT and DMI

A second formulation comprises from about 0.1 mg to about 2.5 mg of HECPT dissolved in a formulation containing 20 to 7,000 parts by weight of a pharmaceutically acceptable alcohol and about 20 to 8,000 parts by weight of a formulation of a non-ionic surfactant. Suitable alcohols include dehydrated ethyl alcohol USP with or without benzyl alcohol. Suitable non-ionic surfactants include the polyoxyethylated oils, such as polyoxyethylated vegetable oils, such as castor oil, peanut oil, and olive oil. In a preferred embodiment 0.1 mg to 1.0 mg HECPT per ml of formulation consists of 500 to 10,000 parts by weight of dimethylisosorbide, 20 to 8,000 parts by weight of Cremaphor EL (polyoxyethylated castor oil) , 20 to 7,000 parts by weight of ethyl alcohol and 1 to 1,000 parts by weight of total solution weight of citric acid.

Example 3

Oral Formulation of HECPT and DMI

An oral formulation of HECPT in soft gelatin capsules (comprised of gelatin/glycerin/sorbitol/purifiers/purified water) containing HECPT in a final concentration of 0.1 to 1.0 mg per ml in a formulation containing 500 to 10,000 parts of dimethylisosorbide by weight of total solution, citric acid 1 to 1,000 parts by weight, glycerin 1 to 1,000 parts by weight, and polyethylene glycol 300 or polyethylene glycol 400 20 to 8,000 parts by weight, ethyl alcohol 20 to 7,000 parts by weight, sodium acetate 0.1 to 250 parts by weight, pluronic F-127 poloxamer 0.1 to 800 parts by weight, and taurocholic acid 10 to 2,500 parts by weight of total solution weight. The soft gelatin capsules may also be composed of any of a number of compounds used for this purpose including, for example, a mixture of gelatin, glycerin, sorbitol, purified water, and parabens.

Example 4

Formulation #1 of HECPT and DMA

For injection or infusion into aqueous body fluids, a formulation comprises from about 0.1 to about 5.0 mg of HECPT dissolved in 500 to 10,000 parts by weight of total solution weight of dimethylacetamide (DMA), about 1 to about 1,000 parts by weight of a pharmaceutically acceptable acid, about 20 to about 7,000 parts by weight of an alcohol, about 20 to about 8,000 parts by weight of a polyether glycol including polyethylene glycol, and about 20 to about 8,000 parts of a non-ionic surfactant. Suitable pharmaceutically acceptable acids include citric acid, hydrochloric acid and phosphoric acid alone or in any combination. Suitable alcohols include dehydrated ethyl alcohol, benzyl alcohol. Suitable polyether glycols, which can be used individually or in any combination include polyethylene glycol 200, polyethylene glycol 300, polyethylene glycol 400 and propylene glycol. Suitable non-ionic surfactants include polysorbate-80. In a preferred embodiment, the formulation of HECPT is supplied as an intravenous injectable in a sealed unit dose vial comprising a sterile, non-aqueous solution of drug in a vehicle comprising ethyl alcohol, benzyl alcohol, citric acid, polyethylene glycol 300, and polysorbate (Tween 80) in an acidified medium with a pH of 3 to 4 containing HECPT at a final concentration of 0.2 mg per ml.

Example 5

Formulation #2 of HECPT and DMA

A second formulation contains about 0.1 mg to about 5.0 mg of HECPT dissolved in 500 to about 10,000 parts by weight of dimethylacetamide, 1 to 1,000 parts by weight of citric acid, 20 to 7,000 parts by weight of an alcohol and about 20 to 8,000 parts by weight of a non-ionic surfactant. Suitable alcohols include dehydrated ethyl alcohol USP or dehydrated ethyl alcohol and benzyl alcohol. Suitable non-ionic surfactants include the polyoxyethylated oils, such as polyoxyethylated vegetable oils, such as castor oil, peanut oil, and olive oil. In a preferred embodiment 0.1 to 5 mg HECPT is formulated in 500 to 10,000 parts by weight of dimethylacetamide (DMA), 20 to 8,000 parts by weight of Cremaphor EL (polyoxyethylated castor oil), 20 to 7,000 parts by weight dehydrated ethyl alcohol USP, and 50 to 750 parts by weight of citric acid to adjust the final pH between 3 to 4.

Example 6

Oral Formulation of HECPT and DMA

An oral formulation of HECPT in soft gelatin capsules (comprised of gelatin/glycerin/sorbitol/purifiers/purified water) containing 0.1 to 15 mg of HECPT dissolved or suspended in 500 to 10,000 parts of dimethylacetamide, citric acid 1 to 1,000 parts by weight, glycerin 1 to 1,000 parts by weight, and polyethylene glycol 300 or polyethylene glycol 400 20 to 8,000 parts by weight, dehydrated ethyl alcohol 20 to 7,000 parts by weight, sodium acetate 0.1 to 250 parts by weight, pluronic F-127 poloxamer 0.1 to 800 parts by weight, and taurocholic acid 10 to 2,500 parts by weight. The soft gelatin capsules may also be composed of any of a number of compounds used for this purpose including, for example, a mixture of gelatin, glycerin, sorbitol, purified water, and parabens.

Example 7

Administration of HECPT and DMA or DMI Formulations

To allow a prolonged parenteral infusion of HECPT to patients with cancer for clinical infusions, the drug may diluted in 5% Dextrose in water (D5W) to a final concentration of 0.001 mg/ml to about 0.01 mg/ml of HECPT prior to injection or infusion.

Maintaining an acidic pH (3 to 4) in the formulation is particularly important to reduce the slow conversion of HECPT lactone to the E-ring-hydrolyzed carboxylate form, which occurs at physiological pH. At equilibrium under physiologic pH, the ratio of the open-ring carboxylate form to lactone form increases. Hydrolysis of the HECPT lactone E-ring will be substantially reduced if the drug is kept in an acidic environment. Some of the unpredictable toxicity seen in earlier clinical trials using sodium camptothecin may have been due to the formation of greater amounts of the lactone form of camptothecin, which is 10-fold more toxic than sodium camptothecin in mice. The lactone form of camptothecin, as in HECPT, is less water soluble than the carboxylate E-ring form. When early clinical trials were first conducted with camptothecin formulated using NaOH, the significance of maintaining the closed lactone E ring for uniform efficacy in treating patients with cancer was poorly understood. The early reported unpredictable clinical toxicities associated with camptothecin administration may have been exacerbated by the NaOH formulation which promotes the formation of the carboxylate form, and by the relative lack of understanding of the significance of the lactone form of camptothecin as it relates to antitumor activity.

Example 8

Solubility of Camptothecin in Various Solvents

This Example was designed to test the solubility of camptothecin, which is used as a reference compound for 7-ethyl-10-hydroxy camptothecin in different solvents. For this Example, BNPI-1028 is camptothecin. The solubility of camptothecin was tested in water, ethanol, benzyl alcohol, propylene glycol, PEG 300, DMI and DMA. For this Example, the maximum amount of camptothecin that would dissolve in 1 ml of the indicated solvent at 4° C. or at 25° C. was measured. For example, referring to Table 4, 0.928 mg camptothecin dissolved in 1 ml of DMI at 25° C., 5.0 mg camptothecin was dissolved in 1 ml of DMA at 25° C., while only 0.051 mg camptothecin dissolved in 1 ml of ethanol (200 proof) 25° C. See Table 4 below. See Table 4. The numbers in the Parentheses are greater than highest calibration standard. They are considered acceptable because of the linear response of the method.

This Example confirmed the poorly water soluble nature of camptothecin and demonstrated that camptothecin is relatively insoluble in water and polar solvents (i.e. ethanol, propylene glycol). This Example also showed that camptothecin was much more soluble in non-polar solvents such as benzyl alcohol, dimethyl isosorbide and dimethylacetamide. From this data, it can be concluded that maximum dissolution of camptothecin depends on the temperature (4° C. versus 25° C.) and solvent. As is evident, camptothecin dissolves better in DMI and DMA than in ethanol or water. Also, camptothecin is much more soluble in DMA than in DMI.

TABLE 4

Solubility of Camptothecin in DMA or DMI in Different Solvents

| Solvent | Target Concentration (µg/mL) | 4° C. Actual Concentration (µg/mL) | 25° C. Actual Concentration (µg/mL) |
| --- | --- | --- | --- |
| Milli - Q Water | 2620 | 0.7 | 0.2 |
| Ethanol (200 Proof) | 2620 | 41 | 51 |
| Benzyl Alcohol | 2710 | (2663) | 1674 |
| Propylene Glycol | 3150 | 236 | 281 |
| PEG 300 | 2660 | 650 | (706) |
| Dimethylisosorbide | 2460 | 510 | 928 |
| N,N-Dimethyl Acetamide | 10000 | 5500 | 5000 |

Example 9

Solubility of HECPT in DMA with Additional Components (Range in Parts by Weight)

This Example was designed to determine the range in parts by weight for a variety of different components added to an initial solution of HECPT and DMA. Table 5 is a compilation of these ranges. Various combinations of the components are presented in Tables 6, 7, and 8.

TABLE 5

SOLUBILITY OF SN38 (0.1 MG/ML TO 10 MG/ML) IN DMA WITH ADDITIONAL COMPONENTS (RANGE IN PARTS BY WEIGHT)

| COMPONENT | RANGE IN PARTS BY WEIGHT | TABLE NUMBER |
| --- | --- | --- |
| Dimethylacetamide (DMA) | 500–10,000 | 6, 7, 8 |
| Total Acid | 1–3,500 | 6, 7, 8 |
| Citric Acid | 1–1,000 | 6, 7, 8 |
| Taurocholic Acid | 10–2,500 | 8 |
| PEG 300, PEG 400 | 20–8,000 | 7, 8 |

TABLE 5-continued

SOLUBILITY OF SN38 (0.1 MG/ML TO 10 MG/ML)
IN DMA WITH ADDITIONAL COMPONENTS
(RANGE IN PARTS BY WEIGHT)

| COMPONENT | RANGE IN PARTS BY WEIGHT | TABLE NUMBER |
|---|---|---|
| Glycerin | 1–1,000 | 8 |
| Benzyl Alcohol | 20–4,000 | 6 |
| Dehydrated Ethyl Alcohol USP (Ethanol) | 20–7,000 | 6, 7, 8 |
| Polysorbate - 80 | 20–8,000 | 6 |
| Cremaphor EL (Polyoxyethylated castor oil) | 20–8,000 | 7 |
| Propylene Glycol | 20–8,000 | |
| Poloxamer (Poloxamer 127) | 0.1–800 | 8 |
| Sodium Acetate | 0.1–250 | 8 |

Example 10

Modified Parenteral Formulation Version 1
HECPT with DMA

This Example presents one preferred parenteral formulation of HECPT and DMA in combination with a variety of different components. For each formulation approximately 2.5 mg of HECPT was dissolved in 1000 parts of a pure form of DMA at 25° C. Dissolution was achieved with gentle agitation until a clear solution resulted within about 2 hours. Approximately one hundred (100) parts of a mineral acid is added to this solution of HECPT and DMA to obtain a final pH of between 2 and 6. A more preferred pH range is between 3 and 4. Examples of mineral acids are pure hydrochloric acid (0.1N) and phosphoric acid. These are examples only and not intended to be the only mineral acids used in this invention. Range of HECPT in DMA is 0.1 mg to 0.25 mg HECPT per ml of formulation.

Example 11

Modified Parenteral Formulation Version 1
HECPT with DMA

This Example presents another preferred parenteral formulation of HECPT and DMA in combination with a variety of different components. For each formulation approximately 2.5 mg of HECPT was dissolved in 1000 parts of a pure form of DMA at 25° C. Dissolution was achieved with gentle agitation until a clear solution resulted within about two hours. About five hundred (500) parts of a carboxylic acid is added to this solution of HECPT and DMA. Examples of carboxylic acids are tartaric acid, citric acid, succinic, fumaric, maleic acid, gluconic acid, ascorbic acid, taurocholic acid, and taurocholic acid in an admixture with citric acid. These are examples only and not intended to be the only carboxylic acids for this invention.

Examples of different combinational parenteral formulations are presented in Table 6 below. This parenteral formulation includes between about 0.1 to about 0.25 mg per ml of HECPT per ml of formulation, ethanol (about 20 to about 7,000 parts by weight), benzyl alcohol (about 500 to about 5,000 parts by weight), citric acid (about 1 to about 1,000 parts by weight), polyethylene glycol 300 (PEG 300: about 20 to about 8,000 parts by weight), DMA (also called DMAC: about 500 to about 10,000 parts by weight) and Tween 80 (polysorbate-80, a non-ionic surfactant: about 20 to about 8,000 parts by weight).

TABLE 6

Modified Oral or Parenteral Formlation Version 1 (with DMAC)

| Formulation Number | Ethanol Nominal (mL) | Ethanol Exact (mL) | Benzyl Alcohol Nominal (mL) | Benzyl Alcohol Exact (mL) | Citric Acid Nominal (G) | Citric Acid Exact (G) | PEG 300 Nominal (G) | PEG 300 Exact (G) | DMAC Nominal (mL) | DMAC Exact (mL) | Tween 80 Nominal (G) | Tween 80 Exact (G) |
|---|---|---|---|---|---|---|---|---|---|---|---|---|
| 4 - DMAC | 6.337 | 6.337 | — | — | 1.0000 | 1.0077 | 50.0000 | 49.9909 | 10.684 | 10.684 | 10.0000 | 10.0097 |
| 9 - DMAC | 1.901 | 1.901 | — | — | 1.5000 | 1.5085 | 15.0000 | 15.0179 | 32.051 | 32.051 | 30.0000 | 29.9929 |
| 10 - DMAC | 20.279 | 20.279 | 3.444 | 3.444 | 4.0000 | 3.9962 | 40.0000 | 40.2157 | 8.547 | 8.547 | 8.0000 | 8.0297 |

Example 12

Modified Parenteral Formulation Version 2

HECPT with DMA

This Example presents yet another preferred parenteral formulation of HECPT and DMA in combination with a variety of different components. For each formulation approximately 2.5 mg of HECPT was dissolved in 1000 parts of a pure form of DMA at 25° C. Dissolution was achieved with gentle agitation until a clear solution resulted within about two hours. About five hundred (500) parts of a carboxylic acid is added to this solution of HECPT and DMA. Examples of carboxylic acids are tartaric acid, citric acid, succinic, fumaric, maleic acid, gluconic acid, ascorbic acid, taurocholic acid, and taurocholic acid in an admixture with citric acid. These are examples of carboxylic acids only and not intended to be the only carboxylic acids for this invention.

Examples of different combinational parenteral formulations are presented in Table 7 below. This parenteral formulation contains HECPT between about 0.1 to about 0.25 mg per ml, ethanol (about 20 to about 7,000 parts by weight), citric acid (about 1 to 1,000 parts by weight), DMA (also called DMAC: about 500 to about 10,000 parts by weight) and Cremaphor EL (20–8,000 parts by weight).

TABLE 7

Modified Oral or Parenteral Formulation Version 2 (with DMAC)

| Formulation Number | Cremaphor EL | | Ethanol | | Citric Acid | | DMAC | |
|---|---|---|---|---|---|---|---|---|
| | Nominal (G) | Exact (G) | Nominal (mL) | Exact (mL) | Nominal (G) | Exact (G) | Nominal (mL) | Exact (mL) |
| 1 | 40.0000 | 39.9927 | 25.349 | 25.349 | 4.0000 | 4.0000 | 42.735 | 42.735 |
| 2 | 100.0000 | 100.0010 | 6.337 | 6.337 | 5.0000 | 5.0008 | 10.684 | 10.684 |
| 3 | 10.0000 | 10.0100 | 6.337 | 6.337 | 5.0000 | 5.0012 | 106.838 | 106.838 |
| 9 | 4.0000 | 4.0458 | 50.697 | 50.697 | 2.0000 | 2.0010 | 42.735 | 42.735 |

Example 13

Oral Formulations—Version 2

HECPT with DMA

This Example a preferred oral formulation of HECPT and DMA in combination with a variety of different components. For each formulation approximately 2.5 mg of HECPT was dissolved in 1000 parts of a pure form of DMA at 25° C. Dissolution was achieved with gentle agitation until a clear solution resulted within about two hours. About five hundred (500) parts by weight of a carboxylic acid is added to this solution of HECPT and DMA. Examples of carboxylic acids are tartaric acid, citric acid, succinic, fumaric, maleic acid, gluconic acid, ascorbic acid, taurocholic acid, and taurocholic acid in an admixture with citric acid. These are examples of carboxylic acids only and not intended to be the only carboxylic acids for this invention.

Examples of different combinational oral formulations are presented in Table 8 below. This oral formulation contains about 0.1 to about 0.25 mg per ml of HECPT, citric acid (about 1 to about 1,000 parts by weight), glycerin (about 1 to about 1,000 parts by weight), PEG 300 (about 20 to about 8,000 parts by weight), ethanol (about 20 to about 7,000 parts by weight), DMA (: about 500 to about 10,000 parts by weight), A surfactant (Polaxomer 127: about 0.1 to about 800 parts by weight), Sodium Acetate (about 0.1 to about 250 parts by weight), and taurocholic acid (about 10 to about 2,500 parts by weight).

TABLE 8

Oral Formulations - Version 2 (with DMAC and Polaxomer 127)

| Formulation Number | Citric Acid | | Glycerine | | PEG 300 | | Ethanol | |
|---|---|---|---|---|---|---|---|---|
| | Nominal (G) | Exact (G) | Nominal (G) | Exact (G) | Nominal (G) | Exact (G) | Nominal (mL) | Exact (mL) |
| 1* | 10.0000 | 10.0000 | 6.0000 | 6.0269 | 45.0000 | 45.0118 | 10.111 | 10.111 |
| 2 | 0.2000 | 0.2001 | — | — | 36.0000 | 36.5757 | 10.849 | 10.849 |
| 3 | 0.4000 | 0.4001 | — | — | 40.0000 | 40.0169 | 18.276 | 18.276 |
| 4 | 0.1000 | 0.1000 | — | — | 18.0000 | 18.0109 | 10.488 | 10.488 |
| 5* | 6.0000 | 6.0012 | — | — | 15.0000 | 15.0052 | 5.725 | 5.725 |
| 6 | 0.1500 | 0.1503 | 3.6000 | 3.6014 | 15.0000 | 15.2513 | 5.475 | 5.475 |
| 7 | 0.2000 | 0.2023 | 4.8000 | 4.8090 | 20.0000 | 20.0186 | 20.659 | 20.659 |
| 8* | 10.0000 | 10.0029 | 6.0000 | 6.0084 | 45.0000 | 45.0218 | 10.111 | 10.111 |
| 9 | 8.0000 | 8.0002 | — | — | 20.0000 | 20.0190 | 10.139 | 10.139 |
| 10 | 8.0000 | 8.0096 | 4.8000 | 4.8458 | 36.0000 | 36.0201 | 16.793 | 16.793 |
| 11 | 0.1000 | 0.1001 | — | — | 18.0000 | 18.0001 | 10.488 | 10.488 |
| 12 | 0.1000 | 0.1000 | 2.4000 | 2.4169 | 18.0000 | 18.0392 | 7.534 | 7.534 |
| 13 | 2.5000 | 2.5003 | 1.5000 | 1.5247 | 6.2500 | 6.4536 | 9.846 | 9.846 |
| 14 | 0.2000 | 0.2022 | — | — | 36.0000 | 36.0383 | 10.849 | 10.849 |
| 15 | 2.5000 | 2.5017 | — | — | 11.2500 | 11.2540 | 10.579 | 10.579 |
| 16* | 6.0000 | 6.0001 | — | — | 15.0000 | 15.0010 | 5.725 | 5.725 |

| Formulation Number | DMAC | | Polaxomer 127 | | Na Acetate | | Taurocholic A. | |
|---|---|---|---|---|---|---|---|---|
| | Nominal (mL) | Exact (mL) | Nominal (G) | Exact (G) | Nominal (G) | Exact (G) | Nominal (G) | Exact (G) |
| 1* | 5.342 | 5.342 | 5.0000 | 5.0021 | 0.8000 | 0.8055 | — | — |
| 2 | 42.735 | 42.735 | 0.2000 | 0.2025 | 0.6400 | 0.6404 | — | — |
| 3 | 8.547 | 8.547 | 8.0000 | 8.0011 | 1.2800 | 1.2796 | — | — |
| 4 | 2.137 | 2.137 | 2.0000 | 2.0016 | — | — | 11.0000 | 11.0139 |
| 5* | 3.205 | 3.205 | 0.1500 | 0.1501 | — | — | 16.5000 | 16.6039 |

TABLE 8-continued

| | | | | | | | | |
|---|---|---|---|---|---|---|---|---|
| 6 | 3.205 | 3.205 | 0.1500 | 0.1532 | 0.4800 | 0.4802 | 16.5000 | 16.8519 |
| 7 | 42.735 | 42.735 | 0.2000 | 0.1995 | — | — | — | — |
| 8* | 5.342 | 5.342 | 5.0000 | 5.0019 | 0.8000 | 0.8002 | — | — |
| 9 | 42.735 | 42.735 | 4.0000 | 4.0015 | — | — | — | — |
| 10 | 4.274 | 4.274 | 0.2000 | 0.2012 | — | — | — | — |
| 11 | 2.137 | 2.137 | 2.0000 | 2.0069 | — | — | 11.0000 | 11.1143 |
| 12 | 21.368 | 21.368 | 2.0000 | 2.0705 | — | — | 11.0000 | 11.0624 |
| 13 | 13.355 | 13.355 | 1.2500 | 1.2512 | 0.2000 | 0.2003 | 6.8750 | 6.9402 |
| 14 | 42.735 | 42.735 | 0.2000 | 0.2072 | 0.6400 | 0.6401 | — | — |
| 15 | 13.355 | 13.355 | 0.0630 | 0.0628 | 0.2000 | 0.2005 | 6.8750 | 6.8872 |
| 16* | 3.205 | 3.205 | 0.1500 | 0.1508 | — | — | 16.5000 | 16.4333 |

*Prepared with citric acid-monohydrate, all others prepared with citric acid-anhydrous.

Example 14

Solubility of SN38 in DMI with Additional Components (Range in Parts by Weight)

This Example was designed to determine the range in parts by weight for a variety of different components added to an initial solution of HECPT and DMI. Table 9 is a compilation of these ranges. Various combinations of the components are presented in Tables 10, 11, and 12.

TABLE 9

SOLUBILITY OF SN38 (0.1 MG/ML TO 1.0 MG/ML) IN DMI WITH ADDITIONAL COMPONENTS (RANGE IN PARTS BY WEIGHT)

| COMPONENT | RANGE IN PARTS BY WEIGHT | TABLE NUMBER |
|---|---|---|
| Dimethylisosorbide (DMI) | 500–10,000 | 10, 11, 12 |
| Total Acid | 1–3,500 | 10, 11, 12 |
| Citric Acid | 1–1,000 | 10, 11, 12 |
| Taurocholic Acid | 10–2,500 | 12 |
| Polyethylene Glycol (PEG 300 or PEG 400) | 20–8,000 | 10, 12 |
| Propylene Glycol | 20–8,000 | |
| Glycerin | 1–1,000 | 12 |
| Benzyl Alcohol | 20–4,000 | 10 |
| Dehydgated Ethyl Alcohol USP (Ethanol) | 20–7,000 | 10, 11, 12 |
| Polysorbate (Tween 80) | 20–8,000 | 10 |
| Cremaphor EL (Polyoxyethylated castor oil) | 20–8,000 | 11 |
| Ionic Surfactant (Polaxomer 127) | 0.1–800 | 12 |
| Sodium Acetate | 0.1–250 | 12 |

Example 15

Modified Parenteral Formulation Version 1

HECPT with DMI

This Example presents one preferred parenteral formulation of HECPT and DMI in combination with a variety of different components. For each formulation approximately 0.1 to 0.25 mg of HECPT was dissolved in 1000 parts of a pure form of DMI at 25° C. Dissolution was achieved with gentle agitation until a clear solution resulted within about two hours. About one hundred (100) parts by weight of a mineral acid is added to this solution of HECPT and DMI to obtain a final pH of between 2 and 6. A more preferred pH range is between 3 and 4. Examples of mineral acids are pure hydrochloric acid (0.1N) and phosphoric acid. These are examples only and not intended to be the only mineral acids used in this invention. The concentration range of HECPT in this formulation is about 0.1 mg to about 0.25 mg HECPT per ml.

Example 16

Modified Parenteral Formulation Version 1

HECPT with DMI

This Example presents another preferred parenteral formulation of HECPT and DMI in combination with a variety of different components. For each formulation approximately 2.5 mg of HECPT was dissolved in 1000 parts of a pure form of DMI at 25° C. Dissolution was achieved with gentle agitation until a clear solution resulted within about two hours. About five hundred (500) parts by weight of a carboxylic acid is added to this solution of HECPT and DMI. Examples of carboxylic acids are tartaric acid, citric acid, succinic, fumaric, maleic acid, gluconic acid, ascorbic acid, taurocholic acid, and taurocholic acid in an admixture with citric acid. These are examples only and not intended to be the only carboxylic acids for this invention.

Examples of different combinational parenteral formulations are presented in Table 10 below. This parenteral formulation includes 0.1 to about 0.25 mg of HECPT per ml of formulation, ethanol (about 20 to about 7,000 parts by weight), benzyl alcohol (about 20 to about 4,000 parts by weight), citric acid (about 1 to about 1,000 parts by weight), polyethylene glycol 300 (about 20 to about 8,000 parts by weight), DMI (about 500 to about 1,000 parts by weight) and polysorbate-80 (Tween 80, a non-ionic surfactant: about 20 to about 8,000 parts by weight).

TABLE 10

Parenteral or Oral Formulation Version 1 (with DMI)

| Formulation Number | Ethanol | | Benzyl Alcohol | | Citric Acid | | PEG 300 | | DMI | | Tween 80 | |
|---|---|---|---|---|---|---|---|---|---|---|---|---|
| | Nominal (mL) | Exact (mL) | Nominal (mL) | Exact (mL) | Nominal (G) | Exact (G) | Nominal (mL) | Exact (mL) | Nominal (mL) | Exact (mL) | Nominal (G) | Exact (G) |
| 1 | 2.281 | 2.281 | 1.55 | 1.55 | 0.3600 | 0.3601 | 28.75 | 32.4 | 3.13 | 3.13 | 33.3 mL | 33.3 mL |
| 2 | 8.745 | 8.745 | — | — | 0.3450 | 0.3457 | 27.55 | 27.5 | 30.00 | 30.0 | 3.4500 | 3.4644 |
| 3 | 19.011 | 19.011 | 3.23 | 3.3 | 3.7500 | 3.7520 | 33.27 | 33.3 | 6.52 | 6.522 | 7.5000 | 7.6955 |
| 4 | 7.605 | 7.605 | — | — | 1.2000 | 1.2024 | 53.24 | 53.2 | 10.44 | 10.435 | 12.0000 | 11.1000 |
| 5 | 7.605 | 7.605 | 1.29 | 1.3 | 0.3000 | 0.3001 | 13.31 | 13.3 | 26.09 | 26 | 30.0000 | 29.9663 |
| 6 | 8.745 | 8.745 | — | — | 0.3450 | 0.3455 | 27.55 | 27.5 | 30.00 | 30 | 3.4500 | 3.5841 |
| 7 | 8.745 | 8.745 | — | — | 1.7250 | 1.7250 | 27.55 | 27.5 | 3.00 | 3.0 | 34.5000 | 34.4804 |
| 8 | 2.281 | 2.281 | 1.55 | 1.55 | 0.3600 | 0.3605 | 28.70 | 28.7 | 3.13 | 3.13 | 36.0000 | 36.2250 |
| 9 | 1.901 | 1.901 | — | — | 1.5000 | 1.4999 | 13.31 | 13.3 | 26.09 | 26 | 30.0000 | 30.0917 |
| 10 | 19.011 | 19.011 | 3.23 | 3.3 | 3.7500 | 3.7501 | 33.27 | 33.3 | 6.52 | 6.522 | 7.5000 | 7.5530 |
| 11 | 1.901 | 1.901 | — | — | 1.5000 | 1.5011 | 13.31 | 13.3 | 26.09 | 26 | 30.0000 | 30.0215 |
| 12 | 2.281 | 2.281 | 1.55 | 1.55 | 1.8000 | 1.7017 | 28.75 | 28.7 | 31.30 | 31.3 | 3.6000 | 3.6106 |

Example 17

Modified Parenteral Formulation Version 2

HECPT with DMI

This Example presents yet another preferred parenteral formulation of HECPT and DMI in combination with a variety of different components. For each formulation approximately 0.25 mg of HECPT was dissolved in 1000 parts of a pure form of DMI at 25° C. Dissolution was achieved with gentle agitation until a clear solution resulted within about two hours. About five hundred (500) parts of a carboxylic acid is added to this solution of HECPT and DMI. Examples of carboxylic acids are tartaric acid, citric acid, succinic, fumaric, maleic acid, gluconic acid, ascorbic acid, taurocholic acid, and taurocholic acid in an admixture with citric acid. These are examples of carboxylic acids only and not intended to be the only carboxylic acids for this invention.

Examples of different combinational parenteral formulations are presented in Table 11 below. This parenteral formulation includes 0.1 to about 0.25 mg per ml of HECPT, ethanol (20 to 7,000 parts by weight), citric acid (about 1 to about 1,000 parts by weight), DMI (about 500 to about 10,000 parts by weight) and Cremaphor EL (about 20 to about 8,000 parts by weight).

Example 18

Oral Formulations—Version 2

HECPT with DMI

This Example is a preferred oral formulation of HECPT and DMI in combination with a variety of different components. For each formulation approximately 0.25 mg of HECPT was dissolved in 1000 parts of a pure form of DMI at 25° C. Dissolution was achieved with gentle agitation until a clear solution resulted within about two hours. About five hundred (500) parts by weight of a carboxylic acid is added to this solution of HECPT and DMI. Examples of carboxylic acids are tartaric acid, citric acid, succinic, fumaric, maleic acid, gluconic acid, ascorbic acid, taurocholic acid, and taurocholic acid in an admixture with citric acid. These are examples of carboxylic acids only and not intended to be the only carboxylic acids for this invention.

Examples of different combinational oral formulations are presented in Table 12 below. This oral formulation includes 0.1 to about 0.25 mg of HECPT per ml, citric acid (about 1 to about 1,000 parts by weight), glycerin (about 1 to about 1,000 parts by weight), polyethylene glycol 300 (PEG 300: about 20 to about 8,000 parts by weight), ethanol (about 20 to about 7,000 parts by weight), DMI (about 500 to about 10,000 parts by weight), a surfactant (Polaxomer 127:0.1 to

TABLE 11

Parenteral or Oral Formulation Version 2 (with DMI)

| Formulation Number | Cremaphor EL | | Ethanol | | Citric Acid | | DMI | |
|---|---|---|---|---|---|---|---|---|
| | Nominal (G) | Exact (G) | Nominal (mL) | Exact (mL) | Nominal (G) | Exact (G) | Nominal (mL) | Exact (mL) |
| 1 | 40.0000 | 39.9939 | 25.349 | 25.350 | 4.0000 | 4.0007 | 34.783 | 34.783 |
| 2 | 100.0000 | 100.0850 | 6.337 | 6.337 | 5.0000 | 5.0013 | 8.696 | 8.7 |
| 3 | 10.0000 | 9.9343 | 6.337 | 6.337 | 5.0000 | 5.0001 | 86.957 | 87 |
| 4 | 4.0000 | 4.0099 | 50.697 | 50.7 | 2.0000 | 2.0005 | 34.783 | 34.783 |
| 5 | 30.0000 | 30.0684 | 38.023 | 38 | 0.3000 | 0.3000 | 26.087 | 26.1 |
| 6 | 40.0000 | 39.9942 | 25.349 | 25.35 | 4.0000 | 3.9997 | 34.783 | 34.8 |
| 7 | 30.0000 | 30.1973 | 38.023 | 38 | 0.3000 | 0.3234 | 26.087 | 26 |
| 8 | 6.0000 | 6.7330 | 76.046 | 76 | 0.6000 | 0.6010 | 5.217 | 5.217 |
| 9 | 4.0000 | 4.0018 | 50.697 | 50.7 | 2.0000 | 2.0004 | 34.783 | 34.8 |
| 10 | 40.0000 | 39.9882 | 50.697 | 50.7 | 2.0000 | 2.0000 | 3.478 | 3.5 |
| 11 | 50.0000 | 49.9857 | 3.169 | 3.16 | 0.5000 | 0.5019 | 43.478 | 43.5 |
| 12 | 100.0000 | 100.0470 | 6.337 | 6.337 | 5.0000 | 5.0013 | 8.696 | 8.7 | about 800 parts by weight), sodium acetate (about 0.1 to about 250 parts by weight), and taurocholic acid (about 10 to about 2,500 parts by weight).

and Tumor Inhibitor from Camptotheca Accuminata, J. Am. Chem. Soc., 88, 3888, 1966.

TABLE 12

Oral Formulation - Version 1 (with DMI and Polaxomer 68)

| Formulation Number | Citric Acid | | Glycerine | | PEG 300 | | Ethanol | |
|---|---|---|---|---|---|---|---|---|
| | Nominal (G) | Exact (G) | Nominal (G) | Exact (G) | Nominal (G) | Exact (G) | Nominal (mL) | Exact (mL) |
| 1 | 10.0000 | 10.0132 | 6.0000 | 6.0484 | 45.0000 | 45.1421 | 10.111 | 10.111 |
| 2 | 0.2000 | 0.2045 | — | — | 36.0000 | 36.5490 | 10.849 | 10.849 |
| 3 | 0.4000 | 0.4019 | — | — | 40.0000 | 40.0001 | 18.276 | 18.276 |
| 4 | 0.1000 | 0.1003 | — | — | 18.0000 | 18.0706 | 10.488 | 10.488 |
| 5* | 6.0000 | 15.0036 | — | — | 15.0000 | 15.0766 | 5.725 | 14.316 |
| 6* | 0.1500 | 0.3995 | 3.6000 | 3.6017 | 15.0000 | 15.0050 | 5.475 | 14.582 |
| 7 | 0.2000 | 0.2005 | 4.8000 | 4.8596 | 20.0000 | 20.1606 | 20.659 | 20.659 |
| 8 | 10.0000 | 10.0125 | 6.0000 | 5.9997 | 45.0000 | 44.9950 | 10.111 | 10.111 |
| 9 | 8.000 | 8.0083 | — | — | 20.0000 | 20.0880 | 10.139 | 10.139 |
| 10 | 8.0000 | 7.9995 | 4.8000 | 4.8743 | 36.0000 | 35.9995 | 16.793 | 16.793 |
| 11 | 0.1000 | 0.1011 | — | — | 18.0000 | 18.0057 | 10.488 | 10.488 |
| 12* | 0.1000 | 0.1506 | 2.4000 | 2.4393 | 18.0000 | 18.0398 | 7.534 | 11.301 |
| 13* | 2.5000 | 6.0028 | 1.5000 | 1.5152 | 6.2500 | 6.6421 | 9.846 | 23.630 |
| 14 | 0.2000 | 0.2001 | — | — | 36.0000 | 36.0393 | 10.849 | 10.849 |
| 15* | 2.5000 | 5.0038 | — | — | 11.2500 | 11.5865 | 10.579 | 21.158 |
| 16* | 6.0000 | 15.0002 | — | — | 15.0000 | 15.0224 | 5.725 | 14.312 |

| Formulation Number | DMI | | Polaxomer 68 | | Na Acetate | | Taurocholic A. | |
|---|---|---|---|---|---|---|---|---|
| | Nominal (mL) | Exact (mL) | Nominal (G) | Exact (G) | Nominal (G) | Exact (G) | Nominal (G) | Exact (G) |
| 1 | 4.348 | 4.348 | 5.0000 | 5.0041 | 0.8000 | 0.7968 | — | — |
| 2 | 34.783 | 34.783 | 0.2000 | 0.2106 | 0.6400 | 0.6446 | — | — |
| 3 | 6.957 | 6.957 | 8.0000 | 8.0086 | 1.2800 | 1.2869 | — | — |
| 4 | 1.739 | 1.739 | 2.0000 | 1.9992 | — | — | 11.0000 | 11.0033 |
| 5* | 2.609 | 2.609 | 0.1500 | 0.1526 | — | — | 16.5000 | 16.5011 |
| 6* | 2.609 | 2.609 | 0.1500 | 0.1522 | 0.4800 | 0.4867 | 16.5000 | 16.5025 |
| 7 | 34.783 | 34.783 | 0.2000 | 0.2010 | — | — | — | — |
| 8 | 4.348 | 4.348 | 5.0000 | 5.0025 | 0.8000 | 0.8256 | — | — |
| 9 | 34.783 | 34.783 | 4.0000 | 4.0045 | — | — | — | — |
| 10 | 3.478 | 3.478 | 0.2000 | 0.2074 | — | — | — | — |
| 11 | 1.739 | 1.739 | 2.0000 | 2.0018 | — | — | 11.0000 | 11.0118 |
| 12* | 17.391 | 17.391 | 2.0000 | 2.0039 | — | — | 11.0000 | 11.0041 |
| 13* | 10.870 | 10.870 | 1.2500 | 1.2548 | 0.2000 | 0.2144 | 6.8750 | 6.8741 |
| 14 | 34.783 | 34.783 | 0.2000 | 0.2026 | 0.6400 | 0.6414 | — | — |
| 15* | 10.870 | 10.870 | 0.0630 | 0.0616 | 2.0000 | 0.2076 | 6.8750 | 6.8765 |
| 16* | 2.609 | 2.609 | 0.1500 | 0.1515 | — | — | 16.0000 | 16.5052 |

*These formulations were prepared by adding the exact amounts of citric acid to ethanol as described. The nominal quantity of this solution was transferred to another volumetric flask and the remaining excipients added.

REFERENCES

U.S. patents

| | | |
|---|---|---|
| 4,399,276 | 8/1983 | Miyasaka et al. |
| 4,399,282 | 8/1983 | Miyasaka et al. |
| 4,473,692 | 9/1984 | Miyasaka et al. |
| 4,545,880 | 10/1985 | Miyasaka et al. |
| 4,604,463 | 8/1986 | Miyasaka et al. |
| 4,778,891 | 10/1988 | Tagawa et al. |
| 5,061,800 | 10/1991 | Miyasaka et al. |

FOREIGN PATENTS

| | |
|---|---|
| AI4-139,18705/1992 | Seigo et al. |
| AJ63-238,0981?1988 | Takashi et al. |
| AK3-232,88810/1991 | Seigo et al. |
| AL61-85,1904/1986 | Teruo et al. |

Other Publications

Wall, M. E. et al., Plant Antitumor Agents I. Isolation and Structure of Camptothecin, a Novel Alkalloidal Leukemia Barilero et al., Simultaneous Determination of the Camptothecin Analogue CPT-11 and Its Active Metabolite SN38 by High Performance Liquid Chromatography: Application to Plasma Pharmacokinetic Studies in Cancer Patients. J. Chromat. 575: 275–280; 1992.

Clavel, M. et al., Phase I Study of the Camptothecin Analogue CPT-11, Administered Daily for 3 Consecutive Days. Proc. Amer. Assoc. Cancer Res. 3:83, 1992.

Creaven, P. J. et al., Plasma Camptothecin (NSC-100880) Levels During a 5-Day Course of Treatment: Relation to Dose and Toxicity. Cancer Chem. Rep. 56: 573–578, 1972.

Culine, S., Phase I Study of the Camptothecin Analog CPT-11, Using a Weekly Schedule. Proc. of Amer. Soc. Clin. Onc. 11:110, 1992.

Emerson, D. L., In Vivo Antitumor Activity of Two New Seven-substituted Water-soluble Camptothecin Analogues. Cancer Research. 55: 603–609, 1995.

Fukuoka, M. et al., A Phase II Study of CPT-11, A New Derivative of Camptothecin, for Previously Untreated Small-Cell Lung Cancer. J. Clin. Onc. 10(1):16–20, 1992.

Giovanella B C. et al., *DNA Topoisomerase I—Targeted Chemotherapy of Human Colon Cancer in Xenografts.* Science 246: 1046–1048; 1989.

Gottlieb, J. A. et al., *Preliminary Pharmacologic and Clinical Evaluation of Camptothecin Sodium (NSC-100880).* Cancer Chem. Rep. 54: 461–470, 1970.

Gottlieb, J. A. et al., *Treatment of Malignant Melanoma With Camptothecin (NSC-100880).* Cancer Chem. Rep. 56: 103–105, 1972.

Gupta, E., et al., *Metabolic Fate of Irinotecan in Humans: Correlation of Glucuronidation with Diarrhea.* Cancer research 54:1723–1725; 1994.

Haas, N. B. et al., *Phase I/Pharmacokinetic Study of Topotecan by 24, Hour Continuous Infusion Weekly.* Cancer Research 54:1220–1226; 1994.

Hinz, H. R., et al., *Pharmacokinetics of the in Vivo and in Vitro Conversion of 9-Nitro-20(S)-camptothecin to 9-Amino-20(S)-camptothecin in Humans, Dogs, and Mice.* Cancer Research 54:3096; 1994

Hsiang et al., *Arrest of Replication Forks by Drug-stabilized Topoisomerase I-DNA Cleavable Complexes as a Mechanism of Cell Killing by Camptothecin Analogues.* Cancer Res. 49:5077–5082, 1989.

Houghton, P. J. et al., *Therapeutic Efficacy of the Topoisomerase I Inhibitor 7-Ethyl-10-(4-[1-piperidino]-1-piperidino)-carbonyloxy-camptothecin against Human Tumor Xenografts: Lack of Cross-Resistance in Vivo in Tumors with Acquired Resistance to the Topoisomerase I Inhibitor 9-Dimethylaminomethyl-10-hydroxycamptothecin.* Cancer Res. 53:2823–2829, 1993.

Jaxel, C. et al., *Structure Activity Study of the Actions of Camptothecin Derivatives on Mammalian Topoisomerase I: Evidence for a Specific Receptor Site and a relation to Antitumor Activity.* Cancer Res. 49:1465–1469, 1989.

Kaneda, N. et al., *Metabolism and Pharmacokinetics of the Camptothecin Analogue CPT-11 in the Mouse.* Cancer Research 50:1715–1720, 1990.

Kano Y, et al., *Effects of CPT-11 in Combination with other Anti-Cancer Agents in Culture.* Int. J. Cancer 50:604–610;1992.

Kanzawa F, et al., *Role of Carboxylesterase on Metabolism of Camptothecin Analog (CPT-11) in Non-Small Cell Lung Cancer Cell Line PC-7 and C-9 Cells (Meeting Abstract).* Proc. Annual Meet. Am. Assoc. Cancer Res. 33:A2552; 1992.

Kawato, Y. et al., *Intracellular Roles of SN38, a Metabolite of the Camptothecin Derivative CPT-11, in the Antitumor Effect of CPT-11.* Cancer Res. 51:4187–4191, 1991.

Kunimoto, T. et al., *Antitumor Activity of 7-Ethyl-10-[4-(1-piperidino)-1-piperidino] Carbonyloxy-Camptothecin, a Novel Water Soluble Derivative of Camptothecin Against Murine Tumors.* Cancer Res. 47:5944–5947, 1987.

Luzzio, M. J., et al., *Synthesis and Antitumor Activity of Novel Water Soluble Derivatives of Camptothecin as Specific Inhibitors of Topoisomerase I.* J. Med. Chem. 38: 395–401, 1995.

Malone et al., *Desoxycholic Acid Enhancement of Orally Administered Reserpine.* Journal of Pharmaceutical Sciences, 55:972–974 (1966).

Masuda, N. et al., *CPT-11: A New Derivative of Camptothecin for the Treatment of Refractory or Relapsed Small-Cell Lung Cancer.* J. Clin. Onc. 10(8):1225–1229 1992.

Moertel, C. G. et al., *Phase II Study of Camptothecin (NSC-100880) in the Treatment of Advanced Gastrointestinal Cancer.* Cancer Chem. Rep. 56: 95–101, 1972.

Muggia, F. M. et al., *Phase I Clinical Trial of Weekly and Daily Treatment with Camptothecin (NSC-100880): Correlation with Preclinical Studies.* Cancer Chem. Rep. 56: 515–521, 1972.

Negoro, S. et al., *Phase I Study of Weekly Intravenous Infusions of CPT-11, a New Derivative of Camptothecin, in the Treatment of Advanced Non-Small Cell Lung Cancer.* JNCI 83(16): 1164–1168, 1991.

Negoro, S. et al., *Phase II Study of CPT-11, New Camptothecin Derivative, in Small Cell Lung Cancer.* Proc. of Amer. Soc. Clin. Onc. 10:241, 1991.

Niimi S, et al., *Mechanism of Cross-Resistance to a Camptothecin Analogue (CPT-11) in a Human Ovarian Cancer Cell Line Selected by Cisplatin.* Cancer Res. 52:328–333; 1992.

Ohe, Y. et al., *Phase I Study and Pharmacokinetics of CPT-11 with 5-Day Continuous Infusion.* JNCI 84(12) :972–974, 1992.

Ohno, R. et al., *An Early Phase II Study of CPT-11: A New Derivative of Camptothecin, for the Treatment of Leukemia and Lymphoma.* J. Clin. Onc. 8(11):1907–1912, 1990.

Pantazis, P. et al., *Cytotoxic Efficacy of 9-Nitrocamptothecin in the Treatment of Human Malignant Melanoma Cells in Vitro.* Cancer Research. 54: 771–776, 1994.

Pommier, Y. et al., *Camptothecins: Mechanism of Action and Resistance (Meeting Abstract).* Cancer Investigation, Presented at the "Chemotherapy Foundation Symposium X Innovative Cancer Chemotherapy for Tomorrow," page 3, 1992.

Potmesil, M. *Camptothecins: From Bench Research to Hospital Wards.* Cancer Research 54:1431–14391; 1994.

Potmesil, M. et al., *Preclinical and Clinical Development of DNA Topoisomerase I Inhibitors in the United States.* in Andoh, T., Ikeda, H. Oguro, M. (eds): Molecular Biology of DNA Topoisomerases and Its Application to Chemotherapy. Boca Raton, Fla., CRC Press, Inc. 301–311, 1993.

Rivory, L. P., et al., *Kinetics of the in Vivo Interconversion of the Carboxylate and Lactone Forms of Irinotecan (CPT-11) and of Its Metabolite SN-38 in Patients.* Cancer Research. 54:6330–6333, 1994.

Rothenberg, M. L. et al., *A Phase I and Pharmacokinetic Trial of CPT-11 in Patients with Refractory Solid Tumors.* Amer. Soc. Clin. Onc. 11:113, 1992.

Rothenberg, M. L., Kuhn, J. G., Burris, H. A., Nelson, J., Eckardt, J. R., Tristan-Morales, M., Hilsenbeck, S. G., Weiss, G. R., Smith, L. S., Rodriguez, G. I., Rock, M. K., Von Hoff, D. D. *Phase I and Pharmacokinetic Trial of Weekly CPT-11.* Journal of Clinical Oncology. 11:2194–2204 (1993).

Rowinsky, E. et al., *Phase I Pharmacologic Study of CPT-11, A Semisynthetic Topoisomerase I-Targeting Agent, on a Single-Dose Schedule (Meeting Abstract).* Proc. of Amer. Soc. Clin. Onc. 11:115, 1992.

Rowinsky, E. et al., *Phase I and Pharmacological Study of the Novel Topoisomerase I Inhibitor 7-Ethyl-10-[4-(1-piperidino)-1-piperidino] carbonyloxycamptothecin (CPT-11) Administered as a Ninety-Minute Infusion Every 3 Weeks.* Cancer Research 54:427–436; 1994.

Sawada S. et al., *Synthesis and Antitumor Activity of 20 (S) -Camptothecin Derivatives: Carbonate-Linked, Water Soluble, Derivatives of 7-Ethyl-10-hydroxycamptothecin.* Chem. Pharm. Bull. 39:14446–1454; 1991.

Shimada, Y. et al., *Phase II Study of CPT-11, New Camptothecin Derivative, In the Patients with Metastatic Colorectal Cancer.* Proc. of Amer. Soc. Clin. Onc. 10:135, 1991.

Supko, J. G. et al., *Pharmacokinetics of the 9-Amino and 10,11-Methylenedioxy Derivatives of Camptothecin in Mice.* Cancer Res. 53: 3062–3069, 1993.

Takeuchi, S. et al., *Late Phase II Study of CPT-11, A Topoisomerase I Inhibitor, In Advanced Cervical Carcinoma (CC)* (Meeting Abstract). Proc. of Amer. Soc. Clin. Onc. 11:224, 1992.

Wall, M. E. et al., *Camptothecin and Taxol: Discovery to Clinic-Thirteenth Bruce F. Cain Memorial Award Lecture.* Cancer Research. 55:753–760, 1995.

Wall, M. E. et al., *Camptothecin*, in Cassady J M, Douros J D (eds): Anticancer Agents Based on Natural Product Models San Diego, Calif., Academic Press, 1980, 417–436.

Wall, M. E. et al., Plant Antitumor Agents. 30.[1a, b] *Synthesis and Structure Activity of Novel Camptothecin Analogs.* J. Med. Chem., 36:2689–2700 (1993).

Westergaard et al., *The Mechanism Whereby Bile Acid Micelles Increase the Rate of Fatty Acid and Cholesterol Uptake Into the Intestinal Mucosal Cell.* Journal of Clinical Investigation, 58: 97–108 (1976)).

The foregoing description has been directed to particular embodiments of the invention in accordance with requirements of the Patent Statutes for the purposes of illustration and explanation. It will be apparent, however, to those skilled in this art, that many modifications, changes and variations in the claimed antitumor compositions, solutions, methods of administration of the antitumor compositions set forth will be possible without departing from the scope and spirit of the claimed invention. It is intended that the following claims be interpreted to embrace all such modifications and changes.

What is claimed is:

1. A pharmaceutical formulation consisting essentially of:
   a) 7-ethyl-10-hydroxy camptothecin; and
   b) dimethylisosorbide.

2. The pharmaceutical formulation of claim 1 and further including one or more pharmaceutically acceptable carriers, excipients or diluents.

3. The pharmaceutical formulation of claim 1 and further including a pharmaceutically acceptable acid, said acid present in sufficient quantities to maintain the pH of the formulation from about 2.0 to 6.0.

4. The pharmaceutical formulation of claim 3 wherein said pharmaceutically acceptable acid includes an organic acid selected from the group consisting of tartaric acid, citric acid, succinic acid, fumaric acid, maleic acid, gluconic acid, ascorbic acid, taurocholic acid, and taurocholic acid in an admixture with citric acid.

5. The pharmaceutical formulation of claim 3 wherein said pharmaceutically acceptable acid includes a mineral acid selected from the group consisting of hydrochloric acid and phosphoric acid.

6. The pharmaceutical formulation of claim 4 wherein said pharmaceutically acceptable acid includes an admixture of said organic acid, and a mineral acid selected from the group consisting of hydrochloric acid and phosphoric acid.

7. The pharmaceutical formulation of claim 5 wherein said pharmaceutically acceptable acid includes an admixture of an organic acid selected from the group consisting of tartaric acid, citric acid, succinic acid, fumaric acid, maleic acid, gluconic acid, ascorbic acid, taurocholic acid, and taurocholic acid in an admixture with citric acid, and said mineral acid.

8. The pharmaceutical formulation of claim 2 wherein said pharmaceutically acceptable carriers, excipients and diluents include one or more of the following:
   a) a glycol selected from the group consisting of polyethylene glycol and propylene glycol;
   b) an alcohol;
   c) glycerin;
   d) a buffer;
   e) a non-ionic surfactant;
   f) water; and
   g) parabens.

9. The pharmaceutical formulation of claim 8 wherein said alcohol is ethanol or benzyl alcohol or an admixture thereof, said buffer is sodium acetate, and said non-ionic surfactant is a poloxamer.

* * * * *